United States Patent
Xing

(10) Patent No.: US 11,319,592 B2
(45) Date of Patent: *May 3, 2022

(54) TERT AND BRAF MUTATIONS IN HUMAN CANCER

(71) Applicant: THE JOHNS HOPKINS UNIVERSITY, Baltimore, MD (US)

(72) Inventor: Michael Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 417 days.

This patent is subject to a terminal disclaimer.

(21) Appl. No.: 15/301,041

(22) PCT Filed: Apr. 1, 2015

(86) PCT No.: PCT/US2015/023948
§ 371 (c)(1),
(2) Date: Sep. 30, 2016

(87) PCT Pub. No.: WO2015/153808
PCT Pub. Date: Oct. 8, 2015

(65) Prior Publication Data
US 2017/0022572 A1    Jan. 26, 2017

Related U.S. Application Data

(60) Provisional application No. 62/034,966, filed on Aug. 8, 2014, provisional application No. 61/976,109, filed on Apr. 7, 2014, provisional application No. 61/973,581, filed on Apr. 1, 2014.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

WO    2011-091272 A1    7/2011

OTHER PUBLICATIONS

Liu et al., 'Highly prevalent TERT promoter mutations in aggressive thyroid cancers' Endocrine-Related Cancer, vol. 20, No. 4, pp. 603-610 (2013).
Xing et al. 'TERT promoter mutation corporates with BRAF mutation to promote thyroid cancer recurrence' In: 83rd Annual Meeting of the American Thyroid Association Thyroid, vol. 23, Issue S1, pp. A-115-A-121 (2013).
Healio Endocrine Today, 'TERT promoter and BRAF mutation co-existence defines most aggressive subgroup of PTC' Meeting News Coverage, ATA Annual Meeting 2013 (Nov. 2013).
Liu et al., 'The age- and shorter telomere-dependent TERT promoter mutation in follicular thyroid cell-derived carcinomas' Oncogene, vol. 33, No. 42, pp. 4978-4984 (Epub. Oct. 21, 2013).
Huang et al., 'Highly recurrent TERT promoter mutations in human melanoma' Science, vol. 339, No. 6122, pp. 957-959 (2013).
Alexander, et al., (2012) "Preoperative diagnosis of benign thyroid nodules with indeterminate cytology" New England Journal of Medicine 367 705-715.
Bartolazzi, et al., (2008) "Galectin-3-expression analysis in the surgical selection of follicular thyroid nodules with indeterminate fine-needle aspiration cytology: a prospective multicentre study" Lancet Oncology 9 543-549.
Bose, et al., (2012) "Thyroid fine needle aspirate: a post-Bethesda update" Adv Anat Pathol 19 160-169.
Cooper, et al., (2009) "Revised American Thyroid Association management guidelines for patients with thyroid nodules and differentiated thyroid cancer" Thyroid 19 1167-1214.
Guth, et al., (2009) "Very high prevalence of thyroid nodules detected by high frequency (13 MHz) ultrasound examination" European Journal of Clinical Investigation 39 699-706.
Horn, et al., (2013) "TERT promoter mutations in familial and sporadic melanoma" Science 339 959-961.
Howlader, et al., (2014) SEER Cancer Statistics Review, 1975-2011, National Cancer Institute. Bethesda, MD, http://seer.cancer.gov/csr/1975_2011/, based on Nov. 2013 SEER data submission, posted to the SEER web site, Apr. 2014.

(Continued)

*Primary Examiner* — Jehanne S Sitton
(74) *Attorney, Agent, or Firm* — Johns Hopkins Technology Ventures

(57) ABSTRACT

The present invention relates to the field of cancer. More specifically, the present invention provides methods and compositions related to certain mutations in cancer. In one embodiment, a method for treating a subject having aggressive thyroid cancer comprises the steps of (a) obtaining a biological sample from the subject; (b) performing an assay on the sample obtained from the subject to identify a mutation at 1 295 228 C>T (C228T), corresponding to −124 C>T from the translation start site in the promoter of the telomerase reverse transcriptase (TERT) gene, and a T1799A mutation in the BRAF gene that results in a V600E amino acid change; (c) identifying the subject as having or likely to develop aggressive thyroid cancer if the C228T and V600E mutations are identified; and (d) treating the subject with one or more treatment modalities appropriate for a subject having or likely to develop aggressive thyroid cancer. Similar approaches are applied to other human cancers harboring both BRAF V600E mutation and TERT promoter mutations.

10 Claims, 6 Drawing Sheets

Specification includes a Sequence Listing.

(56) References Cited

OTHER PUBLICATIONS

Jemal, et al., (2011) "Global cancer statistics" CA: A Cancer Journal for Clinicians 61 69-90.

Liu, X., et al., (2014) "TERT promoter mutations and their association with BRAF V600E mutation and aggressive clinicopathological characteristics of thyroid cancer" Journal of Clinical Endocrinology and Metabolism 99 E1130-1136.

Mazzaferri, (1993) "Management of a solitary thyroid nodule" N Engl J Med 328 553-559.

Melo, et al., (2014) "TERT promoter mutations are a major indicator of poor outcome in differentiated thyroid carcinomas" Journal of Clinical Endocrinology and Metabolism 99 E754-765.

Nikiforov, et al., (2011) "Impact of mutational testing on the diagnosis and management of patients with cytologically indeterminate thyroid nodules: a prospective analysis of 1056 FNA samples" Journal of Clinical Endocrinology and Metabolism 96 3390-3397.

Vinagre, et al., (2013) "Frequency of TERT promoter mutations in human cancers" Nature Communications 4 2185.

Xing, et al., (2014) "Association between BRAF V600E mutation and recurrence of papillary thyroid cancer" Journal of Clinical Oncology [In press].

Xing, et al., (2013) "Association between BRAF V600E mutation and mortality in patients with papillary thyroid cancer" JAMA—Journal of the American Medical Association 309 1493-1501.

Xing, et al., (2009) "BRAF mutation testing of thyroid fine-needle aspiration biopsy specimens for preoperative risk stratification in papillary thyroid cancer" Journal of Clinical Oncology 27 2977-2982.

Xing, et al., (2013) "Progress in molecular-based management of differentiated thyroid cancer". Lancet 381 1058-1069.

Xing, et al., (2014) "BRAF V600E and IERT Promoter Mutations Cooperatively Identify the Most Aggressive Papillary Thyroid Cancer With Highest Recurrence" Journal of Clinical Oncology JCO. 2014.55.5094 [Epub ahead of print].

Xing, et al., (2004) "Detection of BRAF mutation on fine needle aspiration biopsy specimens: a new diagnostic tool for papillary thyroid cancer" Journal of Clinical Endocrinology and Metabolism 89 2867-2872.

Xing, et al., (2005) "BRAF mutation predicts a poorer clinical prognosis for papillary thyroid cancer" Journal of Clinical Endocrinology and Metabolism 90 6373-6379.

Xing (2005) "BRAF mutation in thyroid cancer" Endocrine-Related Cancer 12 245-262.

Xing (2007) "BRAF mutation in papillary thyroid cancer: pathogenic role, molecular bases, and clinical implications". Endocrine Reviews 28 742-762.

PTC (ALL TYPES)

PTC (CONVENTIONAL TYPE)

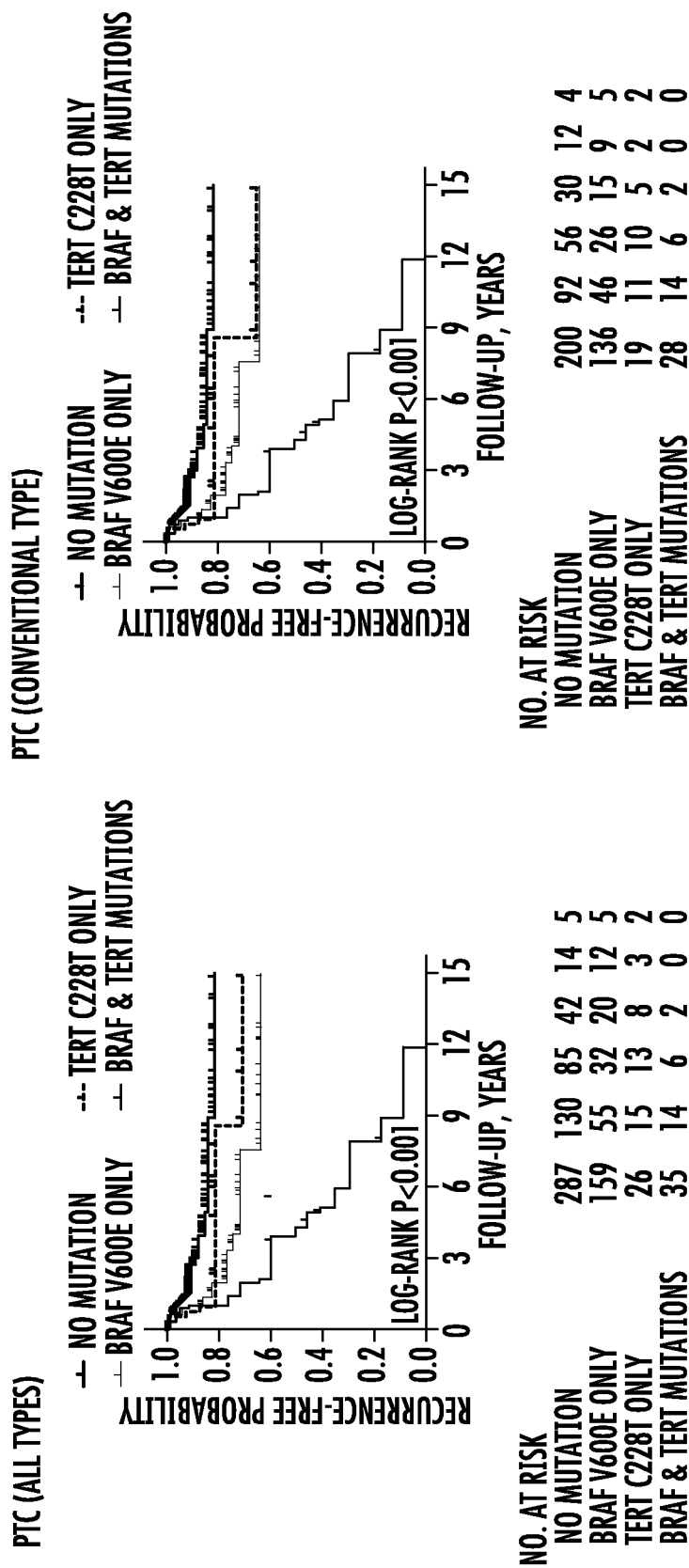

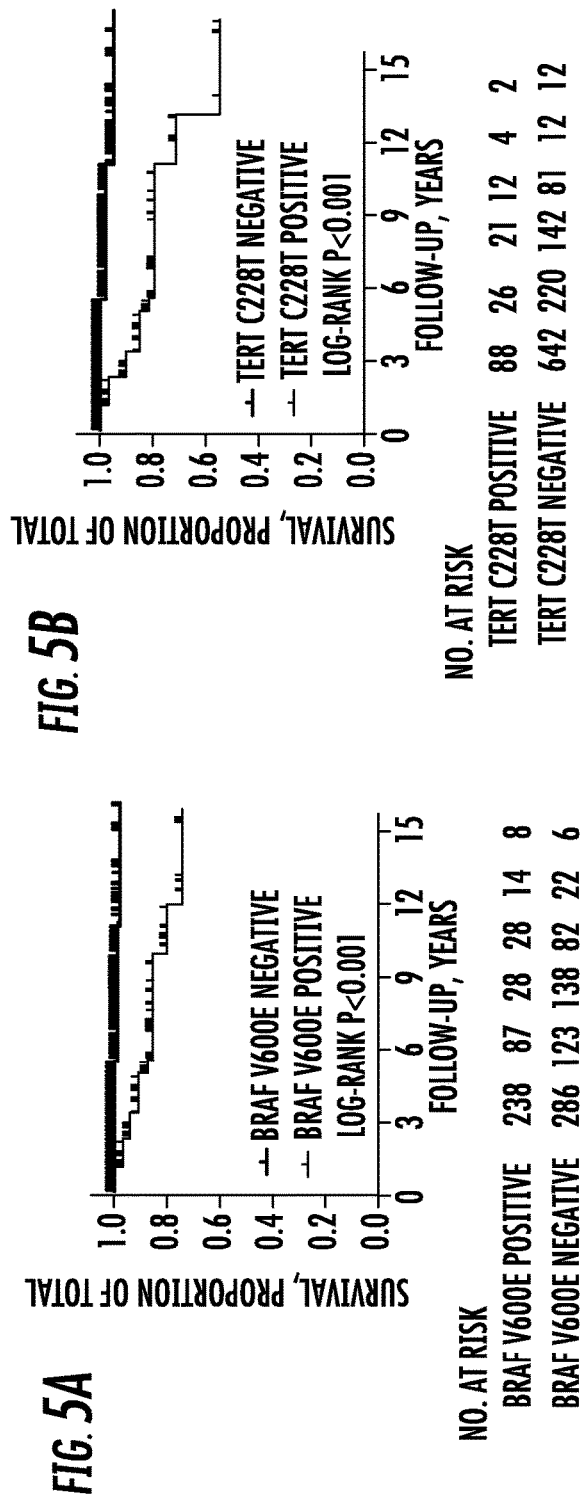
FIG. 5A
FIG. 5B
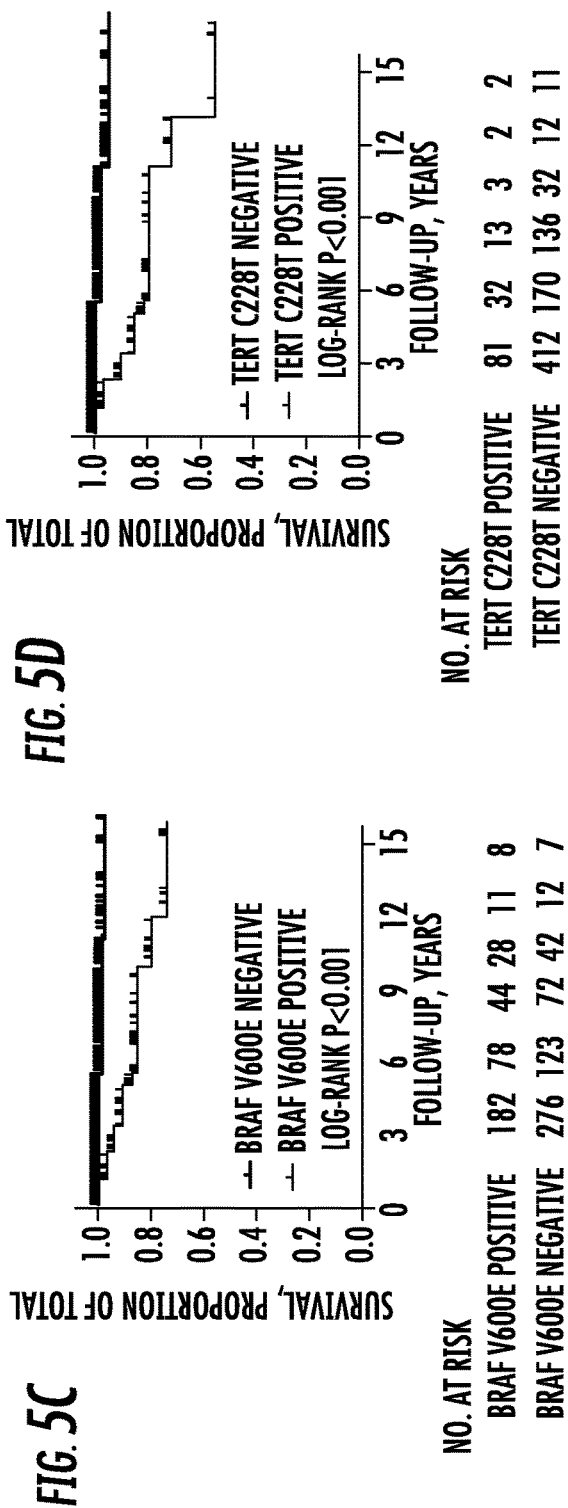
FIG. 5C
FIG. 5D

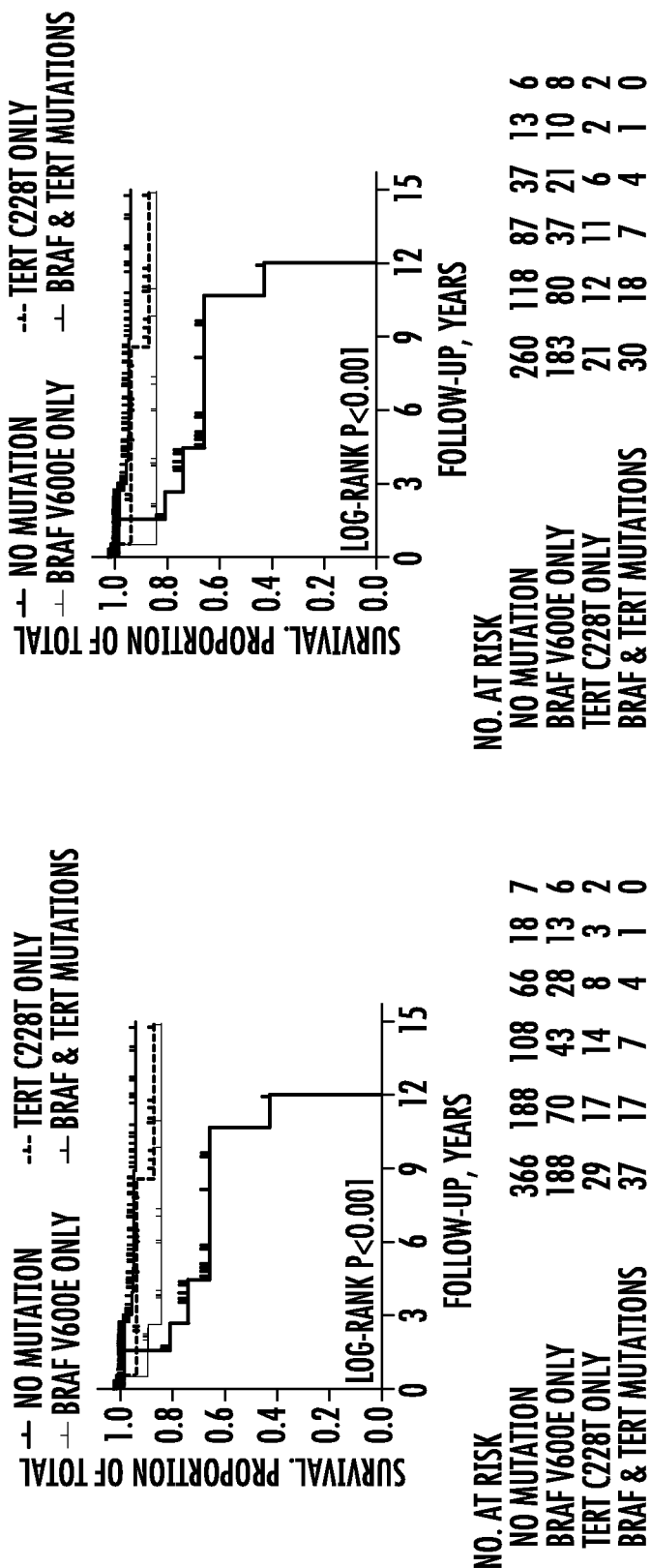

SEQUENCE LISTING

<160> NUMBER OF SEQ ID NOS: 5

<210> SEQ ID NO 1
<211> LENGTH: 11
<212> TYPE: DNA
<213> ORGANISM: Homo sapiens

<400> SEQUENCE: 1
ccccttccgg g                                                             11

<210> SEQ ID NO 2
<211> LENGTH: 20
<212> TYPE: DNA
<213> ORGANISM: Artificial Sequence
<220> FEATURE:
<223> OTHER INFORMATION: TERT promoter sense primer

<400> SEQUENCE: 2
agtggattcg cgggcacaga                                                    20

<210> SEQ ID NO 3
<211> LENGTH: 18
<212> TYPE: DNA
<213> ORGANISM: Artificial Sequence
<220> FEATURE:
<223> OTHER INFORMATION: TERT promoter antisense primer

<400> SEQUENCE: 3
cagcgctgcc tgaaactc                                                      18

<210> SEQ ID NO 4
<211> LENGTH: 23
<212> TYPE: DNA
<213> ORGANISM: Artificial Sequence
<220> FEATURE:
<223> OTHER INFORMATION: BRAF V600E sense primer

<400> SEQUENCE: 4
tcataatgct tgctctgata gga                                                23

<210> SEQ ID NO 5
<211> LENGTH: 22
<212> TYPE: DNA
<213> ORGANISM: Artificial Sequence
<220> FEATURE:
<223> OTHER INFORMATION: BRAF V600E antisense primer

<400> SEQUENCE: 5
ggccaaaaat ttaatcagtg ga                                                 22

TERT AND BRAF MUTATIONS IN HUMAN CANCER

CROSS-REFERENCE TO RELATED APPLICATIONS

This application is a 35 U.S.C. § 371 U.S. national entry of International Application PCT/US2015/023948, having an international filing date of Apr. 1, 2015, which claims the benefit of U.S. Provisional Application No. 61/973,584, filed Apr. 1, 2014, U.S. Provisional Application No. 61/976,109, filed Apr. 7, 2014, and U.S. Provisional Application No. 62/034,966, filed Aug. 8, 2014, the content of each of the aforementioned applications is herein incorporated by reference in their entirety.

STATEMENT OF GOVERNMENTAL INTEREST

This invention was made with government support under grant no. R01CA134225 and grant no. R01CA113507, awarded by the National Institutes of Health. The government has certain rights in the invention.

FIELD OF THE INVENTION

The present invention relates to the field of cancer. More specifically, the present invention provides methods and compositions related to certain mutations in cancer.

INCORPORATION-BY-REFERENCE OF MATERIAL SUBMITTED ELECTRONICALLY

This application contains a sequence listing. It has been submitted electronically via EFS-Web as an ASCII text file entitled "P12971-03_5T25.txt." The sequence listing is 1,259 bytes in size, and was created on Apr. 1, 2015. It is hereby incorporated by reference in its entirety.

BACKGROUND OF THE INVENTION

Papillary thyroid cancer (PTC) is a common endocrine malignancy, which accounts for 80-85% of thyroid malignancies. It can be further classified into conventional variant (CPTC), follicular variant (FVPTC), tall-cell variant (TCPTC) and a few rare other variants, among which CPTC is the most common. Although PTC is highly curable in general, about 10% of cases are destined for a progressive disease course with aggressive tumor behaviors and high disease recurrence and mortality rates. This wide spectrum of disease behaviors often creates dilemmas in clinical risk stratification and decision making on the management of PTC. The aggressive group of PTC poses a particularly difficult prognostic and therapeutic challenge. It is suggested that novel molecular-based management would help tackle this challenge, but, the molecular mechanisms, particularly the genetic backgrounds, remain to be better defined for the aggressiveness of this special group of PTC.

SUMMARY OF THE INVENTION

The present invention is based, at least in part, on the first demonstration that coexistence of BRAF mutation and TERT promoter mutations is a unique genetic background that defines the most aggressive subgroup of certain human cancers that may harbor both mutations, such as papillary thyroid cancer (PTC). PTC was used in this study as a representative human cancer model to test the hypothesis that co-existence of BRAF and TERT mutations is a unique and powerful genetic mechanism that drives particular aggressiveness of human cancer.

Accordingly, in one aspect, the present invention provides methods of treatment of a subject having thyroid cancer. In one embodiment, a method for treating a subject having aggressive thyroid cancer comprising the steps of (a) obtaining a biological sample from the subject; (b) performing an assay on the sample obtained from the subject to identify a (i) 1 295 228 C>T (C228T) mutation, corresponding to −124 C>T from the translation start site in the promoter of the telomerase reverse transcriptase (TERT) gene, (ii) 1 295 250 C>T (C250T) mutation, corresponding to −146 C>T from the translation start site in the promoter of TERT, and/or (iii) a T1799A mutation in the BRAF gene that results in a V600E amino acid change; (c) identifying the subject as having or likely to develop aggressive thyroid cancer when the C228T, C250T and/or V600E mutations are identified; and (d) treating the subject with one or more treatment modalities appropriate for a subject having or likely to develop aggressive thyroid cancer. In a specific embodiment, the assay of step (b) comprises sequencing of the TERT promoter region comprising −124 and −146 from the translation start site in the promoter of TERT and sequencing of the BRAF gene that comprises the T1799A nucleotide site.

In another specific embodiment, the assay of step (b) comprises the steps of: (i) extracting DNA from the biological sample; (ii) contacting the DNA with a primer that specifically hybridizes to the TERT gene and a primer that specifically hybridizes to the BRAF gene; (iii) amplifying by polymerase chain reaction (PCR) a region of the TERT gene that comprises −124 and −146 from the translation start site in the promoter of TERT and a region of the BRAF gene that comprises the T1779A nucleotide site; and (iv) sequencing the amplification product to identify the presence of the C228T, C250T and/or the V600E mutation. In certain embodiments, the TERT primer comprises SEQ ID NO:2 and/or SEQ ID NO:3. In particular embodiments, the BRAF primer comprises SEQ ID NO:4 and/or SEQ ID NO:5.

In particular embodiments, the treatment modality for aggressive thyroid cancer comprises one or more of thyroidectomy and radioactive iodine therapy, and combinations thereof. In a further embodiment, the treatment modality comprises administering to the subject a TERT inhibitor or a BRAF mutant inhibitor or a MEK inhibitor (inhibiting the MAP kinase pathway) or the combination of a TERT inhibitor with one of the latter two inhibitors. In yet another embodiment, the aggressive thyroid cancer is papillary thyroid cancer (PTC) and can also be anaplastic thyroid cancer which also harbors BRAF V600E mutation and TERT promoter mutations.

In another embodiment, the present invention provides a method for treating a patient identified as having the C228T and/or C250T and/or BRAF T1799A/V600E mutations. The treatment can comprise an appropriate treatment modality for subject having aggressive thyroid cancer. Such treatments can comprise one or more of thyroidectomy and radioactive iodine therapy, a TERT inhibitor, a BRAF mutant inhibitor, a MEK inhibitor and all combinations of the foregoing. In certain embodiments, the aggressive thyroid cancer is papillary thyroid cancer (PTC) or anaplastic thyroid cancer.

In another aspect, the present invention provides methods of identifying a subject as having or likely to develop aggressive thyroid cancer, and treatment thereof. In one embodiment, a method for identifying a subject as having or likely to develop aggressive thyroid cancer comprising the steps of (a) obtaining a biological sample from the subject; (b) performing an assay on the sample obtained from the subject to identify a (i) 1 295 228 C>T (C228T) mutation, corresponding to −124 C>T from the translation start site in the promoter of the telomerase reverse transcriptase (TERT) gene, (ii) 1 295 250 C>T (C250T) mutation, corresponding to −146 C>T from the translation start site in the promoter of TERT, and/or (iii) a T1799A mutation in the BRAF gene that results in a V600E amino acid change; and (c) identifying the subject as having or likely to develop aggressive thyroid cancer when the C228T, C250T and/or V600E mutations are identified. In a more specific embodiment, the assay of step (b) comprises sequencing of the TERT promoter region comprising −124 and −146 from the translation start site in the promoter of TERT and sequencing of the BRAF gene that comprises the T1799A nucleotide site.

In yet another specific embodiment, the assay of step (b) comprises the steps of (i) extracting DNA from the biological sample; (ii) contacting the DNA with a primer that specifically hybridizes to the TERT gene and a primer that specifically hybridizes to the BRAF gene; (iii) amplifying by polymerase chain reaction (PCR) a region of the TERT gene that comprises −124 and −146 from the translation start site in the promoter of TERT and a region of the BRAF gene that comprises the T1779A nucleotide site; and (iv) sequencing the amplification product to identify the presence of the C228T and the V600E mutation.

In further embodiments, the method further comprises the step of administering a treatment modality appropriate for a subject having or likely to develop aggressive thyroid cancer. In particular embodiments, the treatment modality for aggressive thyroid cancer comprises one or more of thyroidectomy and radioactive iodine therapy, and combinations thereof. In a further embodiment, the treatment modality comprises administering to the subject a TERT inhibitor or a BRAF mutant inhibitor or a MEK inhibitor (inhibiting the MAP kinase pathway) or the combination of a TERT inhibitor with one of the latter two inhibitors. In yet another embodiment, the aggressive thyroid cancer is papillary thyroid cancer (PTC) and can also be anaplastic thyroid cancer which also harbors BRAF V600E mutation and TERT promoter mutations.

In other embodiments, the mutations described herein can be identified in a patient's DNA and an appropriate treatment recommended, administered, or prescribed. In a further embodiment, a sample can be obtained from a patient and a diagnostic test order for identifying the TERT and/or BRAF mutations described herein. In other embodiments, certain treatments can be recommended, prescribed or administered to a patient identified as having the TERT and/or BRAF mutations described herein.

Accordingly, in another aspect, the present invention provides methods of treatment of subject having other cancers that harbor the C228T TERT mutation, C250T TERT mutation, the V600E BRAF mutation and combinations thereof. In yet another aspect, the present invention provides methods of identifying a subject as having or likely to develop aggressive types of other cancers that harbor the C228T TERT mutation, C250T TERT mutation, the V600E BRAF mutation and combinations thereof, and treatment thereof. Examples of such cancers include, but not limited to, melanoma, colon cancer, brain tumor, leukemia (particularly hairy cell leukemia), lungs cancer, ovarian cancer, uterine cancer, cervical cancer, nasopharyngeal cancer, pancreatic cancer, and papillary craniopharyngiomas. Knowledge of BRAF and TERT promoter mutations can help with better risk stratification and prognostication and better management of these cancers as for PTC.

In the methods described herein, the biological sample can be any appropriate sample from which the TERT/BRAF mutations can be detected including, but not limited to, blood, peripheral blood, serum, plasma, cerebrospinal fluid, urine, saliva, stool, synovial fluid and tissue. In certain embodiments, the sample is from a fine needs aspiration biopsy. In other embodiments, the sample is a urine sample.

BRIEF DESCRIPTION OF THE FIGURES

FIG. 1A shows the results on the analyses of patients with PTC of all types. FIG. 1B shows the results on the analyses of conventional variant PTC only. In both FIG. 1A and FIG. 1B, the left panels show the impacts of the BRAF V600E mutation on tumor recurrence-free survival of patients and the right panels show the impacts of the TERT C228T mutation on tumor recurrence-free survivals of patients. In each panel, the blue line represents patients negative for the indicated mutation and the red line represents patients positive for the indicated mutation.

FIGS. 2A and 2B. Kaplan-Meier analyses of the impacts of BRAF V600E or TERT C288T alone or their coexistence on disease-free survival of patients with papillary thyroid cancer (PTC). FIG. 2A shows the results on the analyses of patients with PTC of all types and FIG. 2B shows the results on the analyses of conventional variant PTC only. Four groups of patients are indicated in FIG. 2A or FIG. 2B, including patients with neither mutation (black line), TERT C228T mutation only (green line), BRAF V600E mutation only (blue line), and coexistence of the two mutations (red line).

FIGS. 5A-5D. Association between BRAF V600E or TERT C228T and decreased patient survival. FIGS. 5A and 5B—all PTC. FIGS. 6C and D—Conventional PTC.

FIGS. 6A and 6B. Cooperative effects of BRAF V600E and TERT C228T mutations on decreased patient survival. FIG. 6A—all PTC. FIG. 6B—conventional PTC.

DETAILED DESCRIPTION OF THE INVENTION

Figure 1A:
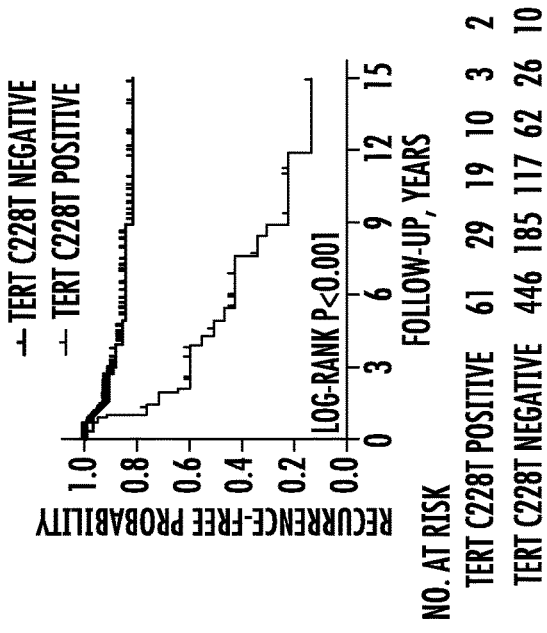
FIGS. 1A and 1B. Kaplan-Meier analyses of the impacts of BRAF V600E and TERT C228T mutations on disease-free survival of patients with papillary thyroid cancer (PTC).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

An "agonist" is a type of modulator and refers to an agent that binds a target and can activate one or more functions of the target. For example, an agonist of a protein can bind the protein and activate the protein in the absence of its natural or cognate ligand.

As used herein, an "antagonist" is a type of modulator and is used interchangeably with the term "inhibitor." In certain non-limiting embodiments, the term refers to an agent that binds a target (e.g., a protein) and can inhibit a one or more functions of the target. For example, an antagonist of an enzymatic protein can bind the protein and inhibit the enzymatic activity of the protein.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against TERT and used as TERT modulators. In other embodiments, antibodies may be raised against BRAF and used as BRAF modulators.

As used herein, the term "effective," means adequate to accomplish a desired, expected, or intended result. More particularly, a "therapeutically effective amount" as provided herein refers to an amount of a TERT and/or BRAF modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a TERT and/or BRAF modulator, necessary to provide the desired therapeutic effect, e.g., an amount that is effective to prevent, alleviate, or ameliorate symptoms of disease or prolong the survival of the subject being treated. In a particular embodiment, the disease or condition is cancer. In a more specific embodiment, the cancer is thyroid cancer. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

The term "inhibitor" is a type of modulator and is used interchangeably with the term "antagonist." The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is TERT. The term also includes agents that have activity in addition to TERT inhibitory activity. In another embodiment, the target gene or protein is BRAF. The term also includes agents that have activity in addition to BRAF inhibitory activity. Examples of BRAF inhibitors include Sorafenib (Bay 43-9006, Nexavar) and Vemurafenib (PLX4032), BDC-0879, PLX-4720, Dabrafenib (Tafinlar), and LGX818. In still another embodiment, the target gene or protein is MEK, a protein downstream BRAF in the BRAF/MEK/MAP kinase pathway (Mitogen-activated protein kinase kinase—also known as MAP2K, MEK, MAPKK). Examples of MEK inhibitors include trametinib, selumetinib (AZD6244), trametinib, CI1040, PD0325901, RDEA119 (refametinib, BAY 869766). In still another embodiment, the combination use of BRAF and TERT inhibitors targeting both genes or proteins is more effective. In still another embodiment, the treatment targets simultaneously TERT and BRAF/MEK using their corresponding inhibitors.

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "TERT modulator" refers to an agent that modulates the expressions and/or activity of TERT. The term "BRAF modulator" refers to an agent that modulates the expressions and/or activity of BRAF. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid;

glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

Optional" or "optionally" means that the subsequently described event or circumstance can or cannot occur, and that the description includes instances where the event or circumstance occurs and instances where it does not.

The terms "patient," "individual," or "subject" are used interchangeably herein, and refer to a mammal, particularly, a human. The patient may have a mild, intermediate or severe disease or condition. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. In particular, the term also includes mammals diagnosed with a BRAF and/or TERT mediated disease, disorder or condition. By "normal subject" is meant an individual who does not have cancer as well as an individual who has increased susceptibility for developing a cancer.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc., and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983).

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for TERT and/or BRAF nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the TERT or BRAF nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

The terms "sample," "patient sample," "biological sample," and the like, encompass a variety of sample types obtained from a patient, individual, or subject and can be used in a diagnostic or monitoring assay. The patient sample may be obtained from a healthy subject or a patient having symptoms associated with prostate cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cord blood, amniotic fluid, cerebrospinal fluid, urine, saliva, stool and synovial fluid), solid tissue samples such as a biopsy specimen or tissue cultures or cells derived therefrom and the progeny thereof. In certain embodiments, a sample comprises blood. In other embodiments, a sample comprises serum. In a specific embodiment, a sample comprises plasma. In yet another embodiment, a semen sample is used. In a further embodiment, a stool sample is used. In particular embodiments, TERT promoter and/or BRAF mutations described here can be tested on tumor tissues, including surgical tissues, needle biopsy tissues (e.g., thyroid nodule needle biopsy specimens), body fluids (e.g., needle biopsy washings, cerebral spinal fluids, urine, etc.) for the diagnosis, prognosis and treatment guidance and treatments of cancer, such as thyroid cancer and other cancers that harbor both the BRAF and TERT mutations described herein. In certain embodiments, the sample is from a fine needle aspiration biopsy.

In certain embodiments, a sample comprises urine. Indeed, TERT mutations can be detected in urine as molecular markers for the diagnosis, prognostication and treatment of bladder cancer. See Hurst et al., 65 European Urology 367-69 (2014) ("Comprehensive Mutation Analysis of the TERT Promoter in Bladder Cancer and Detection of Mutations in Voided Urine"); and Rochakonda et al., 110(43) Proc. Natl. Acad. Sci. USA 17426-17431 (October 2013) ("TERT Promoter Mutations in Bladder Cancer Affect Patient Survival and Disease Recurrence Through Modification by a Common Polymorphism").

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

By "specifically hybridizes" is meant that a probe, primer, or oligonucleotide recognizes and physically interacts (that is, base-pairs) with a substantially complementary nucleic acid (for example, a TERT nucleic acid) under high stringency conditions, and does not substantially base pair with other nucleic acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In a specific embodiment, the disease or condition is cancer. In particular embodiments, the cancer is thyroid cancer. In further embodiments, the cancer includes bladder and glioblastoma.

The terms "TERT-related disease, disorder or condition" or "TERT-mediated disease, disorder or condition," and the like mean diseases, disorders or conditions associated with aberrant TERT activity. In a specific embodiment, the disease or condition is cancer. In general, the term refers to any abnormal state that involves TERT activity. The abnormal state can be due, for example, to a genetic defect.

The terms "BRAF-related disease, disorder or condition" or "BRAF-mediated disease, disorder or condition," and the like mean diseases, disorders or conditions associated with aberrant BRAF activity. In a specific embodiment, the disease or condition is cancer. In general, the term refers to any abnormal state that involves BRAF activity. The abnormal state can be due, for example, to a genetic defect.

II. BRAF V600E and TERT Promoter Mutations as Biomarkers

The present inventors have discovered that BRAF V600E and certain mutations in the promoter region of TERT provide a unique genetic background that predict and identify the most aggressive cases of human thyroid cancers. Thyroid cancer can include follicular thyroid cancer (FTC), papillary thyroid cancer (PTC), conventional PTC, follicular variant PTC (FVPTC), tall-cell PTC (TCPTC). In particular embodiments, the mutations are used to predict and identify the most aggressive type of PTC.

Thus, in certain embodiments, the BRAF and TERT promoter mutations can thus be used to identify individuals having or at risk of developing cancer, in particular, aggressive cancer. In further embodiments, the BRAF and TERT promoter mutations can be used to identify individuals at risk for having or developing aggressive thyroid cancer such as TCPTC, PDTC, ATC and PTC. In certain embodiments, the aggressive thyroid cancer is PTC. The mutations can be identified in subjects who have or have not been diagnosed with cancer. In other embodiments, methods and compositions described herein can be used to examine BRAF and TERT promoter mutations other cancers including melanoma, colon cancer, brain tumor, leukemia (particularly hairy cell leukemia), lungs cancer, ovarian cancer, uterine cancer, cervical cancer, nasopharyngeal cancer, pancreatic cancer, and papillary craniopharyngiomas.

In certain embodiments, DNA can be isolated from a biological sample taken from a subject. DNA can be extracted and purified from biological samples using any suitable technique. A number of techniques for DNA extraction and/or purification are known in the art, and several are commercially available (e.g., ChargeSwitch®, MELT™ total nucleic acid isolation system, MagMAX™ FFPE total nucleic acid isolation kit, MagMAX™ total nucleic acid isolation kit, QIAamp DNA kit, OmniPure™ genomic DNA purification system, WaterMaster™ DNA purification kit). Reagents such as DNAzol® and TR1 Reagent® can also be used to extract and/or purify DNA. DNA can be further purified using Proteinase K and/or RNAse.

In further embodiments, primer/probes can be used to amplify a region of the TERT gene that comprises the promoter. More specifically, primers/probes are capable of amplifying the promoter region at 1 295 228 C>T and/or 1 295 250 C>T (termed C228T and C250T respectively), corresponding to −124 C>T and −146 C>T from the translation start site in the promoter of the telomerase reverse transcriptase (TERT) gene. In one embodiment, a primer comprises the nucleic acid sequence shown in SEQ ID NO:2. In another embodiment, a primer comprises the nucleic acid sequence shown in SEQ ID NO:3. A primer set can comprise the nucleic acid sequences shown in SEQ ID NO:2 and SEQ ID NO:3.

In certain embodiments, primer/probes can be used to amplify a region of the BRAF gene comprising the site for the T1799A (V600E) mutation. In one embodiment, a primer comprises the nucleic acid sequence shown in SEQ ID NO:4. In another embodiment, a primer comprises the nucleic acid sequence shown in SEQ ID NO:5. A primer set can comprise the nucleic acid sequences shown in SEQ ID NO:4 and SEQ ID NO:5.

In particular embodiments, a primer is contacted with isolated DNA from the subject under conditions such that the primer specifically hybridizes with the TERT or BRAF genes.

The primer and DNA thus form a primer:DNA complex. In certain embodiments, the hybridization conditions are such that the formation of the primer:DNA complex is the detection step itself, i.e., the complex forms only if the mutation (TERT C228T, TERT C250T and/or BRAF T1799A (V600E)) is present. In other embodiments, the primer:DNA complex is amplified using polymerase chain reaction, the presence (or not) of the mutation is detected. In certain embodiments, the mutations are detected by sequencing.

As described herein, in certain embodiments, the primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length in-between.

Primers specific for amplification of the TERT gene can be designed to produce amplification products that comprise the TERT C228T and/or TERT C250T locus. Similarly, primers for amplification of the BRAF gene can be designed to produce amplification products that comprise the T1799A (V600E) locus. Such amplification products can be of any suitable length including, but not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, and 300 or more nucleotides.

The probes or primers of the present invention can be prepared by conventional techniques well-known to those skilled in the art. For example, the probes can be prepared using solid-phase synthesis using commercially available equipment. Modified oligonucleotides can also be readily prepared by similar methods. The probes can also be synthesized directly on a solid support according to methods standard in the art. This method of synthesizing polynucleotides is particularly useful when the polynucleotide probes are part of a nucleic acid array.

The present invention therefore also provides predictive, diagnostic, and prognostic kits comprising degenerate primers to amplify a target nucleic acid in the TERT and/or BRAF gene and instructions comprising amplification protocol and analysis of the results. The kit can comprise components for performing a PCR amplification of at least one gene comprising TERT and/or BRAF. In one embodiment, the kit comprises primers for producing amplification products that comprise the TERT C228T and/or TERT C250T locus. Similarly, primers for amplification of the BRAF gene can be designed to produce amplification products that comprise the T1799A (V600E) locus. In a specific embodiment, the primers comprise SEQ ID NO:2, SEQ ID NO:3, SEQ ID NO:4 and/or SEQ ID NO:5. In another embodiment, the kit can also comprise a biological collection/storage container. In specific embodiments, the kit comprises positive control DNA, negative control, and/or a master mix for performing PCR amplifications. In another embodiment, the kit comprises components for sequencing the amplified products. In a specific embodiment, the kit comprises a mix for forward/reverse sequencing of amplified PCR products. In certain embodiments, a separate PCR kit and a separate sequencing kit is provided. Alternatively, a kit can comprise components for both PCR amplification and sequencing. The kit can also comprise instructions for carrying out the amplification and/or sequencing protocols.

In more specific embodiments, the kit may alternatively also comprise buffers, enzymes, and containers for performing the amplification and analysis of the amplification products. The kit may also be a component of a screening, diagnostic or prognostic kit comprising other tools such as DNA microarrays. In some embodiments, the kit also provides one or more control templates, such as nucleic acids isolated from normal tissue sample, and/or a series of samples representing different variances in the TERT and/or BRAF gene.

In one embodiment, the kit provides at least one primer capable of amplifying a different region of the TERT gene. The kit also comprises at least one primer capable of amplifying a region of the BRAF gene. The kit may comprise additional primers for the analysis of expression of several gene variances in a biological sample in one reaction or several parallel reactions. Primers in the kits may be labeled, for example fluorescently labeled, to facilitate detection of the amplification products and consequent analysis of the nucleic acid variances.

In one embodiment, more than one mutation/variance can be detected in one analysis. A combination kit will therefore comprise of primers capable of amplifying different segments of the TERT gene. The kit may also comprise primers capable of amplifying segments of another gene(s) including BRAF. The primers may be differentially labeled, for example, using different fluorescent labels, so as to differentiate between the variances. The primers contained within the kit may include primers selected from complementary sequences to the coding sequence of TERT or BRAF.

In certain embodiments, a patient can be diagnosed or identified by adding a biological sample (e.g., blood, serum, urine, etc.) obtained from the patient to the kit and detecting the TERT promoter mutations(s), for example, by a method which comprises the steps of: (i) collecting blood or blood serum from the patient; (ii) separating DNA from the patient's blood; (iii) adding the DNA from patient to a diagnostic kit; and, (iv) detecting (or not) the BRAF and TERT promoter mutation(s). In this exemplary method, primers are brought into contact with the patient's DNA. The formation of the primer:DNA complex can, for example, be PCR amplified and, in some embodiments, sequenced to detect (or not) the BRAF and TERT promoter mutation. In other kit and diagnostic embodiments, blood or blood serum need not be collected from the patient (i.e., it is already collected). Moreover, in other embodiments, the sample may comprise a tissue sample, urine or a clinical sample.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Coexistence of BRAF V600e and TERT Promoter Mutations is a Unique Genetic Background that Predicts and Identifies the Most Aggressive Cases of Human Cancers Purpose: To investigate the prognostic value of BRAF V600E mutation and the TERT promoter mutation chr5:1,295,228C>T (C228T), individually and in their coexistence, in papillary thyroid cancer (PTC).

Patients And Methods: Retrospective study of the relationship of BRAF and TERT C228T mutations with clinicopathological outcomes of PTC in 507 patients (365 women and 142 men), aged 45.9±14.0 years with a median follow-up of 24 months (interquartile 8-78 months).

Results: Co-existing BRAF V600E and TERT C228T mutations were more commonly than individually associated with high-risk clinicopathological characteristics of PTC. Tumor recurrences were 25.8% (50/194) [77.60 (95% CI 58.81-102.38) per 1000 person years] versus 9.6% (30/313) [22.88 (95% CI 16.00-32.72) per 1000 person years] in BRAF mutation-positive versus-negative patients [HR (95% CI) 3.22 (2.05-5.07)] and 47.5% (29/61) [108.55 (95% CI 75.43-156.20) per 1000 person years] versus 11.4% (51/446) [30.21 (95% CI 22.96-39.74) per 1000 person years] in TERT mutation-positive versus-negative patients [HR (95% CI) 3.46 (2.19-5.45)]. Recurrences were 68.6% (24/35) [211.76 (95% CI 141.94-315.94) per 1000 person years] versus 8.7% (25/287) [21.60 (95% CI 14.59-31.97) per 1000 person years] in patients harboring both mutations versus patients harboring neither mutation [HR (95% CI) 8.51 (4.84-14.97)], which remained significant after clinicopathological co-factor adjustments. Disease-free patient survival curves displayed a moderate decline with BRAF V600E or TERT C228T alone but a sharp decline with two coexisting mutations.

Conclusion: Coexisting BRAF V600E and TERT C228T mutations forms a novel genetic background which defines PTC with the worst clinicopathological outcomes, providing unique prognostic and therapeutic implications.

Materials and Methods

Patients and clinicopathological data. The study included 507 patients (365 women and 142 men), aged at 45.9±14.0 years, who were treated with total thyroidectomy for PTC and clinically followed between 1990 and 2012 at Johns Hopkins Hospital with an overall median follow-up time of 24 months (interquartile 8-78 months) after initial treatments. Therapeutic neck dissection and radioiodine ablation were pursued following standard indications and criteria as previously presented. The demographic data are presented in Table 1. Following the institutional review board approval and informed patient consenting, we obtained thyroid tumor for genetic analysis and retrospectively collected clinicopathological data. The pathological diagnoses of PTC in our patients were formally established. Disease stages of PTC were defined based on the American Joint Committee on Cancer staging system. Tumor recurrence was defined by histologically/cytologically/radioiodine radiographically confirmed recurrent/persistent PTC tumor. Follow-up time was defined as the time interval from the initial thyroidectomy to the discovery of disease recurrence or, in cases without disease recurrence, to the most recent clinical follow-up visit. All mutational analyses were performed after the surgical and radioiodine treatments of patients and the genetic results bored no influence on the treatment decision making.

Mutational analyses. Genomic DNA was isolated from primary PTC tumors by standard phenol-chloroform extraction and ethanol precipitation procedures and subjected to classical Sanger sequencing for the detection of BRAF V600E and TERT C228T mutations. For BRAF V600E, the polymerase chain reaction (PCR) protocol and conditions described previously (Xing et al., 90 J. CLIN. ENDOCRINOL. METAB. 6373-79 (2005)) were used to amplify exon 15 of the BRAF gene containing the mutation hot spot, followed by Big dye reaction for Sanger sequencing. For TERT C228T, PCR was used to amplify a fragment of the TERT promoter containing the C228T hot spot (Xing et al., 20 ENDOCR. RELAT. CANCER 603-10 (2013)).

Both the C228T and C250T mutations create an 11-base nucleotide stretch 5'-CCCCTTCCGGG-3' (SEQ ID NO:1). Briefly, a fragment of the TERT promoter was amplified by PCR on genomic DNA using primers 5'-AGTGGAT-TCGCGGGCACAGA-3' (SEQ ID NO:2) (sense) and 5'-CAGCGCTGCCTGAAACTC-3' (SEQ ID NO:3) (antisense). This resulted in a PCR product of 235 bp, containing the sites where mutations C228T and C250T occur in melanomas (Horn et al. 2013, Huang et al. 2013). About 40-50 ng of genomic DNA were used in the PCR, which was carried out with an initial denaturation step at 95° C. for 3 min, followed by ten cycles of 95° C. denaturation for 30 s, 55° C. annealing for 30 s, and 68° C. elongation for 1 min. This was then followed by 30 cycles of the same settings except for elongation for an additional 5 s in each cycle. The PCR was completed with a final elongation step at 68° C. for 7 min. Following quality confirmation of the PCR products by gel electrophoresis, sequencing PCR was carried out using a Big Dye terminator v3.1 cycle sequencing ready reaction kit (Applied Biosystems) and an ABI PRISM 3730 automated next generation genetic analyzer (Applied Biosystems) at the Johns Hopkins' sequencing facility. When a mutation was identified by Big Dye sequencing using the sense primer, the reaction was repeated using the antisense primer to confirm the mutation.

The BRAF V600E mutation was analyzed as described previously (Hu et al. 2006). Briefly, exon 15 of the BRAF gene containing the site for the T1799A (V600E) mutation was PCR-amplified using primers TCAT-AATGCTTGCTCTGATAGGA (SEQ ID NO:4) (sense) and GGCCAAAAATTTAATCAGTGGA (SEQ ID NO:5) (antisense), resulting in a 212 bp product. The PCR settings included one cycle of 95° C. for 5 min; two cycles of 95° C. for 1 min, 60° C. for 1 min, and 72° C. for 1 min; two cycles of 95° C. for 1 min, 58° C. for 1 min, and 72° C. for 1 min; and 35 cycles of 95° C. for 1 min, 56° C. for 1 min, and 72° C. for 1 min, followed by an extension step at 72° C. for 5 min. After quality confirmation by agarose gel electrophoresis, the PCR products were subjected to Big Dye reaction and sequencing analysis as described above for TERT mutations. All the mutations were confirmed using both the sense and antisense primers.

Statistical analyses. Categorical data were summarized with frequencies and percents. Continuous data were summarized with means±standard deviations (if normally distributed) or medians and interquartile ranges (if not normally distributed). Comparisons of categorical variables were performed using the $\chi^2$ test or, for small cell sizes, Fisher's exact test. Independent t-test and Wilcoxon-Mann-Whitney test were used for normally and non-normally distributed continuous variables, respectively. Kaplan-Meier survival curves with log-rank tests and Cox proportional hazards regression analyses, censoring patients at the time of recurrence or, if no recurrence, at the time of last follow-up visit, were used to compare recurrence-free survivals by mutation status. Independent associations of mutations with PTC recurrence were examined by Cox regression analyses. All P values were two sided and a P<0.05 was treated as statistically significant. The analyses were performed using Stata (Stata/SE version 10.1 for windows; Stata Corp, College Station, Tex., USA) and GraphPad Prism (version 6 for Windows; GraphPad Software, Inc., San Diego, Calif., USA).

Results

BRAF V600E and TERT C228T mutations in PTC. We examined BRAF V600E and TERT C228T mutations in 507 cases of PTC, consisting of several variants (Table 2). BRAF V600E was found in 164/383 (42.8%) CPTC, 15/103 (14.6%) FVPTC, 14/19 (73.7%) TCPTC, and 1/2 (50%) columnar PTC, with an overall prevalence of 38.3% (194/507). TERT C228T was found in 47/383 (12.3%) CPTC, 8/103 (7.8%) FVPTC, 5/19 (26.3%) TCPTC, and 1/2 (50.0%) columnar PTC, with an overall prevalence of 12.0% (61/507). A significant association of TERT C228T with BRAF mutation was observed (Table 3). Specifically, on the overall analysis of all PTC, TERT C228T was found in 26/313 (8.3%) BRAF mutation-negative cases versus 35/194 (18.0%) BRAF mutation-positive cases and, conversely, BRAF mutation was found in 159/446 (35.7%) TERT mutation-negative cases versus 35/61 (57.4%) TERT mutation-positive cases [odds ratio (OR) (95% CI):2.43 (1.40-4.21); P=0.001]. A significant association of the two mutations was similarly observed in CPTC (Table 3). Coexistence of BRAF and TERT mutations was found in 35/507 (6.9%) all PTC and 28/383 (7.3%) CPTC (Table 2).

Relationship of BRAF V600E and TERT C228T mutations with clinicopathological outcomes of PTC. On overall analysis of 507 PTC (Table 1), BRAF V600E mutation was found to be significantly associated with several high-risk clinicopathological characteristics, including male sex of the patient, larger tumor size, extrathyroidal invasion, vascular invasion, lymph node metastasis, and stages III/IV. Tumor recurrence was 30/313 (9.6%) [22.88 (95% CI: 16.00-32.72) recurrences per 1000 person years] in BRAF mutation-negative patients versus 50/194 (25.8%) [77.60 (95% CI: 58.81-102.38) recurrences per 1000 person years] in BRAF mutation-positive patients [HR (95% CI): 3.22 (2.05-5.07); P<0.001] (Table 4). Similarly, TERT C228T was significantly associated with these clinicopathological characteristics and additionally older patient age and distant metastatic recurrence (Table 1). Tumor recurrence was 51/446 (11.4%) [30.21 (95% CI: 22.96-39.74) recurrences per 1000 person years] in TERT mutation-negative cases versus 29/61 (47.5%) [108.55 (95% CI: 75.43-156.20) recurrences per 1000 person years] in TERT mutation-positive cases [HR (95% CI): 3.46 (2.19-5.45); P<0.001] (Table 4). The HRs of BRAF V600E and TERT C228T for tumor recurrence were all highly significant, which remained significant after adjustment for patient age and sex and, as may not be unexpected (see Discussion), they lost significance with their 95% CI marginally crossing 1.0 after additional adjustment for aggressive tumor behaviors (Table 4).

Similar results were obtained when analyses were performed only on CPTC (Table 1 and Table 4). For example, both BRAF V600E and TERT C228T mutations were each associated with several high-risk clinicopathological characteristics. Higher tumor recurrence rates and recurrences per 1000 person years were associated with BRAF V600E or TERT C228T mutations. HR (95% CI) of BRAF V600E for tumor recurrence was 3.10 (95% CI: 1.85-5.20) (P<0.001) and HR (95% CI) of TERT C228T for PTC recurrence was 3.32 (95% CI: 2.00-5.52) (P<0.001).

Impacts of BRAF V600E or TERT C228T alone or their coexistence on clinicopathological outcomes of PTC. On the analysis of all PTC (Table 5), in comparison with the group negative for either mutation, BRAF V600E alone was significantly associated with larger tumor size, extrathyroidal invasion, lymph node metastasis, disease stages III/IV, and tumor recurrences. TERT C228T alone was significantly associated with lymph node metastasis and there was an insignificant association with other clinicopathological characteristics. In contrast, coexistence of BRAF V600E and TERT C228T was strongly associated with virtually all the classical high-risk characteristics as well as distant metastatic recurrence. Patients harboring both BRAF and TERT mutations had the highest recurrence as well, which was 24/35 (68.6%) [211.76 (95% CI:141.94-315.94) recurrences per 1000 person years] versus only 25/287 (8.7%) [21.60 (95% CI: 14.59-31.97) recurrences per 1000 person years] in patients harboring neither mutation [HR (95% CI): 8.51 (4.84-14.97); P<0.001] (Table 6).

Similar individual impacts of BRAF V600E and TERT C288T mutations on clinicopathological outcomes were observed in CPTC (Table 5). In comparison with the group negative for either mutation, BRAF V600E was significantly associated with several high-risk clinicopathological characteristics as well as tumor recurrences. The impacts of TERT C228T alone on clinicopathological outcomes were significant for vascular invasion and lymph node metastasis and short of statistical significance for other parameters. In contrast, coexistence of BRAF V600E and TERT C228T was highly associated with virtually all the high-risk clinicopathological characteristics. Tumor recurrence was 20/28 (71.4%) [or 191.85 (95% CI: 123.77-297.36) recurrences per 1000 person years] in patients harboring both mutations versus 18/200 (9.0%) [or 22.23 (95% CI: 14.00-35.28) recurrences per 1000 person years] in patients harboring neither mutation [HR (95% CI): 7.73 (4.07-14.67); P<0.001] (Table 6).

There was an incremental impact of coexisting BRAF and TERT C228T mutations on PTC recurrence over either mutation alone (Table 7). Specifically, on the analysis of all PTC, tumor recurrence was 24/35 (68.6%) [211.76 (95% CI: 141.94-315.94) recurrences per 1000 person years] in patients harboring both mutations versus 26/159 (16.3%) [48.96 (95% CI:33.34-71.91) recurrences per 1000 person years] in patients harboring only BRAF mutation [HR (95% CI): 3.62 (2.07-6.33); P<0.001] and 5/26 (19.2%) [32.5 (13.53-78.09) recurrences per 1000 person years] in patients harboring only TERT mutation [HR (95% CI): 6.16 (2.29-16.61); P<0.001]. In fact, PTC recurrence associated with coexisting BRAF and TERT mutations was dramatically higher than the sum of those associated with the two mutations individually, demonstrating a synergistic effect of the two mutations on PTC recurrence. Similar results were also obtained in CPTC (Table 7).

Figure 1B:
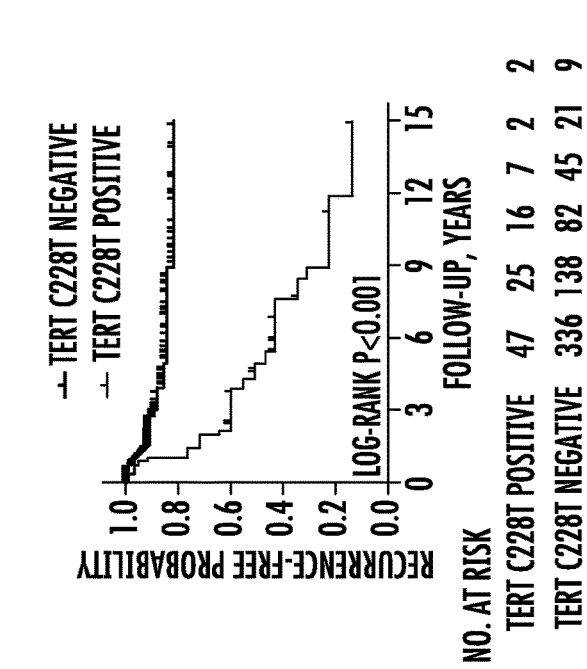
Figure 3:
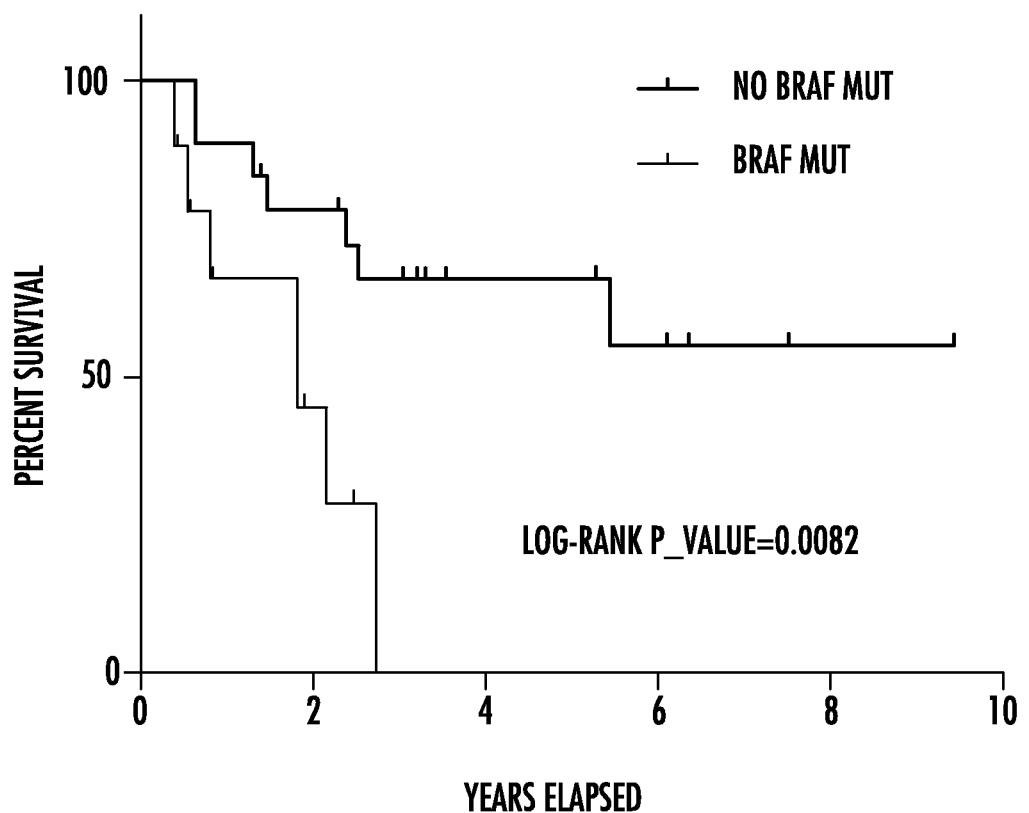
FIG. 3. Kaplan-Meier survival analysis-Significant association of BRAF V600E with decreased survival of patients with melanoma.
Figure 4:
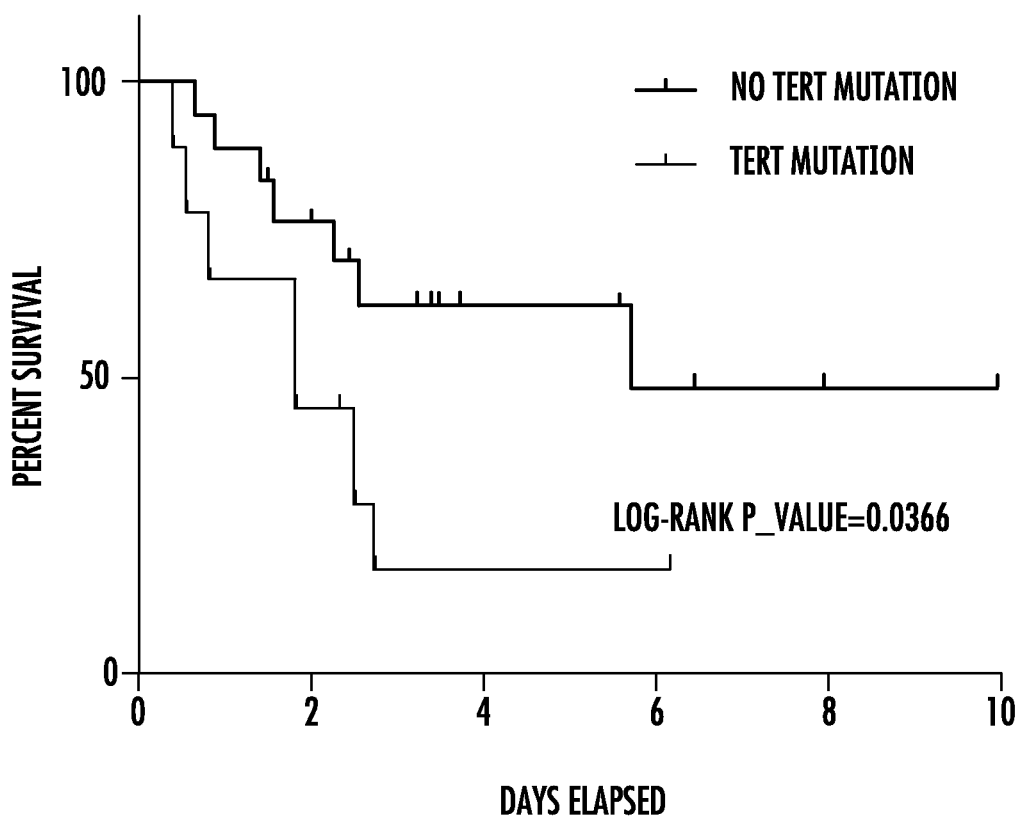
FIG. 4. Kaplan-Meier survival analysis-Significant association of TERT C228T/C250T with decreased survival of patients with melanoma.

Impacts of BRAF V600E and TERT C228T mutations on disease-free survival of patients with PTC. We performed Kaplan-Meier and log-rank analyses of disease-free survivals of patients by genotypes. On analyses of all PTC (FIG. 1A), tumor recurrence-free survival curves had a modest decline in patients negative for BRAF V600E (left panel) or TERT C228T (right panel). They declined further with either the BRAF mutation (left panel) or the TERT mutation (right panel). Similar results were obtained on analyses of CPTC (FIG. 1B).

FIG. 2A shows the impacts of individual BRAF V600E or TERT C228T or their coexistence on tumor recurrence-free survival curves of all PTC patients. There was an increased decline in recurrence-free survival curves from patients with neither mutation, to patients with TERT mutation alone, to patients with BRAF mutation alone, and to patients with both mutations. The curve decline with TERT mutation alone was modest, consistent with the modest effects of the TERT mutation alone on other clinicopathological outcomes (Table 5). The curve decline with coexisting BRAF and TERT mutations was sharp and dramatic, and the curve decline with BRAF mutation alone was intermediate. Virtually identical results were obtained in patients with CPTC (FIG. 2B).

Table 6 summarizes the impacts of BRAF V600E, TERT C228T, and their coexistence on PTC recurrence after adjustment for classical clinicopathological risk factors. HR of BRAF mutation alone for tumor recurrence in all PTC was 2.24 (95% CI: 1.29-3.88), which remained significant at 2.16 (95% CI: 1.24-3.75) after the first adjustment for patient age at diagnosis and sex. This significance was lost after a further additional adjustment for aggressive tumor behaviors, including tumor size, multifocality, extrathyroidal invasion, vascular invasion, and lymph node metastasis. HR of TERT C228T alone for tumor recurrence was not significant, with the 95% CIs all crossing 1.0. In striking contrast, HRs of coexisting BRAF and TERT mutations for tumor recurrence in all PTC was 8.51 (95% CI: 4.84-14.97), which remained significant at 8.41 (95% CI: 4.44-15.94) after the adjustment for patient age and sex and still significant at 3.10 (95% CI: 1.24-7.75) after the additional adjustment for tumor behaviors.

All these HR results for tumor recurrence were similarly obtained in CPTC (Table 6). For example, HRs of coexistence of the two mutations for tumor recurrence of CPTC—unadjusted, adjusted for the first level, and adjusted for the second level—were all significant at 7.73 (95% CI: 4.07-14.67), 7.50 (95% CI: 3.71-15.17), and 4.39 (95% CI: 1.42-13.54), respectively.

Discussion

We have identified a novel genetic background—coexistence of BRAF V600E and TERT C228T mutations—which defines the most aggressive subgroup of PTC. The combined effects of the two mutations on recurrence compared with no mutation remained significant even on multivariate adjustments for the classical clinicopathological risk factors. PTC recurrence with coexisting BRAF and TERT mutations was also significantly higher than that associated with either mutation alone or the sum of the recurrences associated with the two mutations individually, demonstrating an incremental and synergistic effect of the coexisting two mutations. These results were found both in the overall analyses of all PTC and the CPTC variant, establishing coexistence of the two mutations as an important novel genetic background for the worst aggressiveness of PTC.

This cooperative effect of BRAF and TERT promoter mutations can be explained at a molecular level. TERT maintains the length of chromosomes by adding to them telomeres, thus increasing the immortality of cells, and promotes cell proliferation and decrease apoptosis. Transgenic mouse models overexpressing TERT showed increased tumor development and malignant transformation occurred. To be consistent with this oncogenic role of TERT is its common overexpression in human cancers, including thyroid cancer. TERT C228T confers increased transcriptional activities of the TERT promoter by creating consensus binding motifs (GGA[A/T] or CCGGAA) for E-twenty six (ETS)/ternary complex transcription factors. As activation of the MAP kinase pathway up-regulates the ETS system, coexistence of BRAF V600E and TERT C228T forms a unique mechanism up-regulating the expression of TERT. Indeed, coexistence of the two mutations was associated with increased expression of the TERT protein in PTC. This oncogenic cooperation of TERT with BRAF mutation is interestingly similar to the finding in a transgenic mouse model in which p53 mutation and induced overexpression of TERT cooperatively promoted cancer development. To be consistent with the role of TERT C228T in poor clinicopathological outcomes of PTC were also the recent reports of the association of TERT promoter mutations with brain tumor-associated patient mortality, bladder cancer recurrence, and poor laryngeal cancer patient survival.

Many studies have demonstrated a role of BRAF V600E in tumor aggressiveness and even patient mortality in PTC, but some studies failed to do so. In the present study, HRs for tumor recurrence remained significant on the multivariate adjustment for patient age and sex but fell short of significance when aggressive tumor pathological behaviors were adjusted. This statistical result should not be interpreted as the lack of a role of BRAF mutation in the aggressiveness of PTC since, biologically, BRAF mutation uses various molecular mechanisms to promote the aggressive tumor behaviors. As some of these tumor behaviors, particularly lymph node metastases, are the main source of PTC recurrence, it is not surprising that statistical adjustment for them could artificially (and misleadingly) diminish or even null the effect of BRAF mutation on recurrence. The present study represents the largest uniform series of PTC to examine this role of BRAF mutation, but perhaps an even larger study is needed to show an independent role of BRAF mutation. The persistently significant effects of coexisting BRAF and TERT mutations on PTC recurrence after multivariate adjustments for the classical clinicopathological factors do suggest that coexisting BRAF and TERT mutations have a more profound impact.

The effects of TERT C228T fell short of significance when it was separated from BRAF mutation and examined alone, suggesting that TERT mutation needs additional genetic alterations to cooperate to promote the aggressiveness of PTC. We previously reported a particularly high prevalence of TERT C228T in ATC, PDTC, and thyroid cancer cell lines, which were confirmed in several subsequent publications. Thyroid cancer cell lines are usually undifferentiated and commonly harbor multiple genetic alterations, including BRAF mutation. It is thus likely that their aggressiveness is cooperatively driven by coexisting TERT promoter mutations and other genetic alterations, similar to their cooperation found in the present study. Our present results in the American cohort of patients are consistent with our recent similar findings of the impact of coexisting BRAF B600E and TERT promoter mutations on aggressive behaviors of PTC in a Chinese cohort of patients.

The follow-up time of patients in this study was relatively short. However, PTC patients usually present recurrence within the first few years. Therefore, a median of 2 years should have captured the majority of recurrence events of PTC. The disease-free survival curves (FIGS. 1 and 2) show that as time progresses, the separation of the mutation-positive and -negative curves becomes even more prominent, suggesting that in later follow-up years the impact of the mutations on PTC recurrence is even more profound. Therefore, if anything, a median follow-up time of 2 years likely caused an underestimate of the impacts of the BRAF and TERT mutations on PTC recurrence. The follow-up times were different among some groups. However, this variation was corrected by the Cox proportional and regression analyses as these standard statistical methods take the time as a variable into the model. To further correct the time variations, we also additionally report recurrences per 1000 person years.

In summary, this study identifies coexisting BRAF V600E and TERT C228T mutations as a novel genetic background for the most aggressive subgroup of PTC, while the two mutations each alone have relatively less impact on the aggressiveness of PTC. These genetic patterns, by separating PTC patients into different risk groups and by particularly defining the most aggressive group, have important prognostic and therapeutic implications.

TABLE 1

Relationship of BRAF V600E and TERT C228T mutations with clinicopathological outcomes of PTC

| PTC Types | Clinicopathological outcomes | BRAF status | | | TERT status | | |
|---|---|---|---|---|---|---|---|
| | | BRAF V600E | Wild-type BRAF | P value | TERT C228T | Wild-type TERT | P value |
| PTC of all types | Total cases, N | 194 | 313 | | 61 | 446 | |
| | Age at diagnosis (yr) | 47.1 ± 14.4 | 45.2 ± 13.8 | 0.138 | 51.7 ± 15.7 | 45.1 ± 13.6 | <0.001 |
| | Gender (male), n (%) | 69 (35.6) | 73 (23.3) | 0.003 | 32 (52.5) | 110 (24.7) | <0.001 |
| | Tumor size (cm) | 2.0 (1.3-3.0)[12] | 1.7 (1.0-2.8)[9] | 0.003 | 2.3 (1.2-3.5)[6] | 1.8 (1.1-3.0)[15] | 0.048 |
| | Multifocality, n (%) | 68 (36.4)[7] | 122 (39.1)[1] | 0.542 | 20 (33.9)[2] | 170 (38.6)[6] | 0.482 |
| | Extrathyroidal invasion, n (%) | 58 (31.3)[9] | 35 (11.2)[1] | <0.001 | 27 (46.5)[3] | 66 (15.0)[7] | <0.001 |
| | Vascular invasion, n (%) | 36 (20.0)[14] | 41 (13.2)[2] | 0.045 | 14 (25.9)[7] | 63 (14.4)[9] | 0.028 |
| | Lymph node metastasis, n (%) | 85 (46.2)[10] | 68 (21.7) | <0.001 | 31 (52.5)[2] | 122 (27.8)[8] | <0.001 |
| | Distant metastatic recurrence, n (%) | 12 (6.2) | 10 (3.2) | 0.108 | 12 (19.7) | 10 (2.2) | <0.001 |

TABLE 1-continued

Relationship of BRAF V600E and TERT C228T mutations with clinicopathological outcomes of PTC

| PTC Types | Clinicopathological outcomes | BRAF status | | | TERT status | | |
|---|---|---|---|---|---|---|---|
| | | BRAF V600E | Wild-type BRAF | P value | TERT C228T | Wild-type TERT | P value |
| | Disease stage, n (%) | | | | | | |
| | I | 114 (60.6)[6] | 237 (75.7) | | 26 (42.6) | 325 (73.9)[6] | |
| | II | 13 (6.9)[6] | 31 (9.9) | | 6 (9.8) | 38 (8.6)[6] | |
| | III | 39 (20.7)[6] | 35 (11.2) | | 12 (19.7) | 62 (14.1)[6] | |
| | IV | 22 (11.7)[6] | 10 (3.2) | <0.001 | 17 (27.9) | 15 (3.4)[6] | <0.001 |
| | III + IV | 61 (32.4)[6] | 45 (14.4) | <0.001 | 29 (47.5) | 77 (17.5)[6] | <0.001 |
| | Tumor recurrence, n (%) | 50 (25.8) | 30 (9.6) | <0.001 | 29 (47.5) | 51 (11.4) | <0.001 |
| | Total I-131 dose (mCi) | 87.7 (0-100)[16] | 74.9 (0-100)[7] | 0.004 | 100 (29.9-105)[7] | 75 (0-100)[16] | 0.001 |
| | Total follow-up (months) | 18 (7-53) | 31 (8-87) | 0.027 | 30 (12-78) | 24 (6-76) | 0.056 |
| Conventional PTC (CPTC) | Total cases | 164 | 219 | | 47 | 336 | |
| | Age at diagnosis (yr) | 46.7 ± 13.7 | 45.8 ± 13.9 | 0.511 | 51.6 ± 16.0 | 45.4 ± 13.4 | 0.004 |
| | Gender, male, n (%) | 60 (36.6) | 53 (24.2) | 0.009 | 25 (53.2) | 88 (26.2) | <0.001 |
| | Tumor size (cm) | 2 (1.3-3)[12] | 1.5 (0.8-2.3)[9] | <0.001 | 2.3 (1.2-3.5)[6] | 1.6 (1-2.5)[15] | 0.009 |
| | Multifocality, n (%) | 54 (34.4)[7] | 87 (39.9)[1] | 0.277 | 16 (35.6)[2] | 125 (37.9)[6] | 0.763 |
| | Extrathyroidal invasion, n (%) | 48 (31.0)[9] | 29 (13.3)[1] | <0.001 | 23 (52.3)[3] | 54 (16.4)[7] | <0.001 |
| | Vascular invasion, n(%) | 27 (18.0)[14] | 27 (14.4)[2] | 0.140 | 10 (25.0)[7] | 44 (13.5)[9] | 0.052 |
| | Lymph node metastasis, n (%) | 76 (49.0)[9] | 58 (26.5) | <0.001 | 27 (60.0)[2] | 107 (32.5)[7] | <0.001 |
| | Distant metastatic recurrence, n (%) | 7 (4.3) | 8 (3.6) | 0.759 | 8 (17.0) | 7 (2.1) | <0.001 |
| | Disease stage, n (%) | | | | | | |
| | I | 98 (62.0)[6] | 172 (78.5) | | 19 (40.3) | 251 (76.1)[6] | |
| | II | 10 (6.3)[6] | 15 (6.9) | | 3 (6.4) | 22 (6.7)[6] | |
| | III | 32 (20.2)[6] | 23 (10.5) | | 10 (21.3) | 45 (13.6)[6] | |
| | IV | 18 (11.4)[6] | 9 (4.1) | | 15 (31.9) | 12 (3.6)[6] | <0.001 |
| | III + IV | 50 (31.6)[6] | 32 (14.6) | <0.001 | 25 (53.2) | 57 (17.3)[6] | <0.001 |
| | Tumor recurrence, n (%) | 42 (25.6) | 22 (10.0) | <0.001 | 24 (51.1) | 40 (11.9) | <0.001 |
| | Total I-131 dose (mCi) | 75 (0-100)[15] | 51.7 (0-100)[5] | 0.043 | 100 (75-104)[7] | 75 (0-100) | <0.001 |
| | Total follow-up (months) | 19 (6.5-52) | 32 (9-80) | 0.026 | 48 (12-95) | 24 (6-70) | 0.026 |

Footnotes:
Numbers in the right upper corner of each item represent the number of missing cases from the total cases (N); % represents n/(N − missing number) × 100%.

TABLE 2

Impacts of BRAF V600E or TERT C228T or their co-existence on clinicopathological outcomes of PTC

| PTC types | Clinicopathological Outcomes | No mutation | BRAF mutation only | P value | TERT mutation only | P value | BRAF + TERT mutation | P value |
|---|---|---|---|---|---|---|---|---|
| PTC of all types | Total cases, N | 287 | 159 | | 26 | | 35 | |
| | Age at diagnosis (yr) | 45.3 ± 13.7 | 44.8 ± 13.5 | 0.724 | 44.0 ± 14.6 | 0.651 | 57.4 ± 14.1 | <0.001 |
| | Gender, male, n (%) | 65 (22.6) | 45 (28.3) | 0.185 | 8 (30.8) | 0.348 | 24 (68.6) | <0.001 |
| | Tumor size (cm) | 1.7 (1.0-3.0)[7] | 2.0 (1.3-3.0)[8] | 0.044 | 1.8 (1.1-2.5)[2] | 0.885 | 2.7 (1.3-4.0)[4] | 0.002 |
| | Multifocality, n (%) | 114 (39.7) | 56 (36.6)[6] | 0.522 | 8 (32.0)[1] | 0.448 | 12 (35.3)[1] | 0.617 |
| | Extrathyroidal invasion, n (%) | 31 (10.8) | 35 (23.0)[7] | 0.001 | 4 (16.0)[1] | 0.503 | 23 (69.7)[2] | <0.001 |
| | Vascular invasion, n (%) | 35 (12.2)[1] | 28 (18.5)[8] | 0.074 | 6 (24.0)[1] | 0.096 | 8 (27.6)[6] | 0.022 |
| | Lymph node metastasis, n (%) | 58 (20.2) | 64 (42.4)[8] | <0.001 | 10 (38.5) | 0.031 | 21 (63.6)[2] | <0.001 |
| | Distant metastatic recurrence, n (%) | 8 (2.8) | 2 (1.3) | 0.506 | 2 (7.7) | 0.198 | 10 (28.6) | <0.001 |
| | Disease stage, n (%) | | | | | | | |
| | I | 219 (76.3) | 106 (69.3)[6] | | 18 (69.2) | | 8 (22.9) | |
| | II | 27 (9.4) | 11 (7.2)[6] | | 4 (15.4) | | 2 (5.7) | |
| | III | 33 (11.5) | 29 (18.9)[6] | | 2 (7.7) | | 10 (28.6) | |
| | IV | 8 (2.8) | 7 (4.6)[6] | 0.106 | 2 (7.7) | 0.373 | 15 (42.9) | <0.001 |
| | III + IV | 41 (14.3) | 36 (23.5)[6] | 0.015 | 4 (15.4) | 0.776 | 25 (71.4) | <0.001 |
| | Tumor recurrence, n (%) | 25 (8.7) | 26 (16.3) | 0.015 | 5 (19.2) | 0.081 | 24 (68.6) | <0.001 |
| | Total I-131 dose (mCi) | 74.6 (0-100)[5] | 75.4 (0-100)[11] | 0.084 | 77 (0-100)[2] | 0.560 | 100 (98-136)[5] | <0.001 |
| | Total follow-up (months) | 28 (6-85) | 17 (3-52) | 0.048 | 66 (12-116) | 0.030 | 24 (12-60) | 0.864 |
| Conventional PTC(CPTC) | Total cases | 200 | 136 | | 19 | | 28 | |
| | Age at diagnosis (yr) | 46.0 ± 13.7 | 44.7 ± 12.8 | 0.398 | 44.2 ± 16.1 | 0.603 | 56.7 ± 14.2 | <0.001 |
| | Gender, male, n (%) | 47 (23.5) | 41 (30.1) | 0.174 | 6 (31.6) | 0.432 | 19 (67.9) | <0.001 |
| | Tumor size (cm) | 1.5 (0.8-2.3)[7] | 2 (1.3-2.5)[8] | <0.001 | 1.5 (1.0-2.3)[2] | 0.349 | 2.8 (1.7-3.5)[4] | <0.001 |
| | Multifocality, n (%) | 81 (40.5) | 44 (33.8) 6 | 0.223 | 6 (33.3) 1 | 0.552 | 10 (37.0)[1] | 0.730 |

TABLE 2-continued

Impacts of BRAF V600E or TERT C228T or their co-existence on clinicopathological outcomes of PTC

| PTC types | Clinicopathological Outcomes | No mutation | BRAF mutation only | P value | TERT mutation only | P value | BRAF + TERT mutation | P value |
|---|---|---|---|---|---|---|---|---|
| | Extrathyroidal invasion, n (%) | 25 (12.5) | 29 (22.5)[7] | 0.017 | 4 (22.2) 1 | 0.272 | 19 (73.1)[2] | <0.001 |
| | Vascular invasion, n (%) | 21 (10.5)[1] | 23 (18.0)[8] | 0.055 | 6 (33.3) 1 | 0.005 | 4 (18.2)[6] | 0.287 |
| | Lymph node metastasis, n (%) | 49 (24.5) | 58 (45.0)[7] | <0.001 | 9 (47.4) | 0.031 | 18 (29.2)[2] | <0.001 |
| | Distant metastatic recurrence, n (%) | 6 (3.0) | 1 (0.7) | 0.248 | 2 (10.5) | 0.146 | 6 (21.4) | <0.001 |
| | Disease stage, n (%) | | | | | | | |
| | I | 159 (79.5) | 92 (70.8)[6] | | 13 (68.4) | | 6 (21.4) | |
| | II | 13 (6.5) | 9 (6.9)[6] | | 2 (10.5) | | 1 (3.6) | |
| | III | 21 (10.5) | 24 (18.5)[6] | | 2 (10.5) | | 8 (28.6) | |
| | IV | 7 (3.5) | 5 (3.8)[6] | 0.212 | 2 (10.5) | 0.429 | 13 (46.4) | <0.001 |
| | III + IV | 28 (14.0) | 29 (22.3)[6] | 0.051 | 4 (21.0) | 0.492 | 21 (75.0) | <0.001 |
| | Tumor recurrence, n (%) | 18 (9.0) | 22 (16.2) | 0.046 | 4 (21.0) | 0.107 | 20 (71.4) | <0.001 |
| | Total I-131 dose (mCi) | 50.9 (0-100)[3] | 75 (0-100)[10] | 0.193 | 100 (0-103)[2] | 0.110 | 100 (75-131.5)[5] | <0.001 |
| | Total follow-up (months) | 30.5 (8-79) | 17 (2-48.5) | 0.025 | 73 (12-108) | 0.067 | 35.5 (12-61.5) | 0.686 |

Footnotes:
1) Numbers in the right upper corner of each item represent the number of missing cases from the total cases (N); % represents n/(N − missing number) × 100%.
2) P values are from the comparison of the indicated genetic group in the column immediately left to the P value column with the "No mutation" group.

TABLE 3

Hazard Ratios (HR) of BRAF V600E or TERT C228T or their coexistence for the recurrence of PTC

| Type of PTC | Mutations | Recurrence, n/N (%) | Recurrence per 1000 person-years (95% CI) | Hazard ratios (95% CI) Unadjusted | Adjustment 1* | Adjustment 2# |
|---|---|---|---|---|---|---|
| All PTC | No mutation | 25/287 (8.7) | 21.60 (14.59-31.97) | 1.00 | | 1.00 |
| | BRAF mutation only | 26/159 (16.3) | 48.96 (33.34-71.91) | 2.24 (1.29-3.88) | 2.16 (1.24-3.75) | 1.17 (0.62-2.20) |
| | TERT mutation only | 5/26 (19.2) | 32.50 (13.53-78.09) | 1.69 (0.65-4.43) | 1.60 (0.60-4.25) | 0.87 (0.27-2.76) |
| | BRAF + TERT mutations | 24/35 (68.6) | 211.76 (141.94-315.94) | 8.51 (4.84-14.97) | 8.41 (4.44-15.94) | 3.10 (1.24-7.75) |
| CPTC | No mutation | 18/200 (9.0) | 22.23 (14.00-35.28) | 1.00 | | 1.00 |
| | BRAF mutation only | 22/136 (16.2) | 50.25 (33.08-76.31) | 2.20 (1.18-4.11) | 2.06 (1.10-3.86) | 1.03 (0.49-2.15) |
| | TERT mutation only | 4/19 (21.0) | 35.22 (13.22-93.83) | 1.82 (0.61-5.38) | 1.71 (0.56-5.22) | 0.50 (0.12-2.00) |
| | BRAF + TERT mutations | 20/28 (71.4) | 191.85 (123.77-297.36) | 7.73 (4.07-14.67) | 7.50 (3.71-15.17) | 4.39 (1.42-13.54) |

Footnotes:
Hazard ratios and 95% confidential interval (CI) were calculated using Cox regression for the comparison of the indicated mutation group with the group harboring neither mutation ("No mutation").
*Adjustment 1 was made for patient age at diagnosis and sex;
Adjustment 2 was made for patient age at diagnosis, sex, multifocality, tumor size, extrathyroidal invasion, vascular invasion, and lymph node metastasis.
PTC, papillary thyroid cancer;
CPTC, conventional PTC.

TABLE 4

Comparison of PTC recurrence between the "BRAF V600E + TERT C228" group and the BRAF V600E only or TERT C288T only group

| PTC type | Recurrences | (A) BRAF V600E only | (B) TERT C228T only | (C) BRAF + TERT mutations | HR (95% CI), P value Comparison of C with A | Comparison of C with B |
|---|---|---|---|---|---|---|
| All PTC | Recurrence, % (n/N) | 26/159 (16.3) | 5/26 (19.2) | 24/35 (68.6) | | |
| | Recurrence per 1000 person-years (95% CI) | 48.96 (33.34-71.91) | 32.5 (13.53-78.09) | 211.76 (141.94-315.94) | 3.62 (2.07-6.33) P < 0.001 | 6.16 (2.29-16.61) P < 0.001 |
| CPTC | Recurrence, % (n/N) | 22/136 (16.2) | 4/19 (21.0) | 20/28 (71.4) | | |
| | Recurrence per 1000 person-years (95% CI) | 50.25 (33.08-76.31) | 35.22 (13.22-93.83) | 191.85 (123.77-297.36) | 3.30 (1.79-6.06) P < 0.001 | 5.28 (1.76-15.83) P = 0.003 |

Footnotes:
PTC, papillary thyroid cancer;
CPTC, conventional variant PTC;
HR, hazard ratio;
95% CI, 95% confidence interval.

TABLE 5

Prevalence of BRAF V600E and TERT C228T mutations in various variants of PTC

| PTC type | BRAF V600E mutation (n), n/N (%) | TERT C228T mutation (n), n/N (%) | BRAF + TERT mutations (n), n/N (%) |
|---|---|---|---|
| CPTC (N) | 164/383 (42.8) | 47/383 (12.3) | 28/383 (7.3) |
| FVPTC (N) | 15/103 (14.6) | 8/103 (7.8) | 1/103 (1.0) |
| TCPTC (N) | 14/19 (73.7) | 5/19 (26.3) | 5/19 (26.3) |
| Columnar PTC (N) | 1/2 (50.0) | 1/2 (50.0) | 1/2 (50.0) |
| All (N) | 194/507 (38.3) | 61/507 (12.0) | 35/507 (6.9) |

Footnotes:
PTC, papillary thyroid cancer;
CPTC, conventional variant PTC;
FVPTC, follicular variant PTC;
TCPTC, tall-cell variant PTC.

TABLE 6

Association of TERT promoter C228T mutation with BRAF V600E mutation in papillary thyroid cancer

| Tumor type | TERT C228T mutation n/N (%) BRAF− | TERT C228T mutation n/N (%) BRAF+ | BRAE V600E mutation n/N (%) TERT− | BRAE V600E mutation n/N (%) TERT+ | OR (95% CI), |
|---|---|---|---|---|---|
| All PTC | 26/313 (8.3) | 35/194 (18.0) | 159/446 (35.7) | 35/61 (57.4) | 2.43 (1.40-4.21) P = 0.001 |
| CPTC | 19/219 (8.7%) | 28/164 (17.1%) | 136/336 (40.5%) | 28/47 (59.6%) | 2.17 (1.16-4.06) P = 0.013 |

Footnotes:
PTC, papillary thyroid cancer;
CPTC, conventional variant PTC;
95% CI, 95% confidence interval.

TABLE 7

Association of BRAF or TERTC228T promoter mutation with PTC recurrence

| Tumor type | Mutation status | Recurrence, n/N (%) | Recurrence per 1000 person-years (95% CI) | Hazard ratios (95% CI) Unadjusted | Adjusted* | Adjusted# |
|---|---|---|---|---|---|---|
| All PTC | BRAF V600E | | | | | |
| | negative | 30/313 (9.6) | 22.88 (16.00-32.72) | 1.00 | 1.00 | 1.00 |
| | positive | 50/194 (25.8) | 77.60 (58.81-102.38) | 3.22 (2.05-5.07) | 3.02 (1.91-4.77) | 1.51 (0.87-2.60) |
| | TERT C228T | | | | | |
| | negative | 51/446 (11.4) | 30.21 (22.96-39.74) | 1.00 | 1.00 | 1.00 |
| | positive | 29/61 (47.5) | 108.55 (75.43-156.20) | 3.46 (2.19-5.45) | 3.21 (2.02-5.09) | 1.78 (0.97-3.25) |
| CPTC | BRAF V600E | | | | | |
| | negative | 22/219 (10.0) | 23.82 (15.69-36.18) | 1.00 | 1.00 | 1.00 |
| | positive | 42/164 (25.6) | 77.48 (57.26-104.84) | 3.10 (1.85-5.20) | 2.88 (1.71-4.86) | 1.46 (0.77-2.75) |
| | TERT C228T | | | | | |
| | negative | 40/336 (11.9) | 32.06 (23.52-43.71) | 1.00 | 1.00 | 1.00 |
| | positive | 24/47 (51.1) | 110.18 (73.85-164.38) | 3.32 (2.00-5.52) | 3.15 (1.89-5.24) | 1.54 (0.76-3.12) |

Footnotes:
Hazard ratios and 95% confidential interval (CI) were calculated with Cox regression with adjustment
*for patient age at diagnosis and sex or
for patient age at diagnosis, sex, multifocality, tumor size, extrathyroidal invasion, vascular invasion, and lymph node metastasis.
PTC, papillary thyroid cancer;
CPTC, conventional PTC.

Example 2: Significant Association Between TERT C228/250T Promoter Mutations and BRAF V600E Mutations in Melanoma—Coexistence of the Mutations in the Two Genes

TABLE 8

Association of TERT C228/250T with BRAF V600E mutations in melanoma

| TERT C228/250T, n/N (%) | | BRAF V600E, n/N (%) | | |
|---|---|---|---|---|
| BRAF− | BRAF+ | TERT− | TERT+ | |
| 17/44 (38.6) | 16/25 (64) | 9/36 (25) | 16/33 (48.5) | P = 0.04 |

Association of TERT promoter and BRAF mutations with patient mortality in melanoma. Notes on Tables 9-11: "0", negative for the event; "1", positive for the event.

In the analysis presented below in Table 9, the patients were separated into two groups—one, positive for BRAF mutation; two, negative for BRAF mutation. Compared with group one, group two had a marginal association with patient death, demonstrating a marginally significant predictive power of BRAF mutation for patient mortality in melanoma.

TABLE 9

| Group number | BRAF status | Patient death or not (No.) 1 | Patient death or not (No.) 0 | P value |
|---|---|---|---|---|
| One | 0 | 8 | 12 | |
| Two | 1 | 9 | 2 | 0.057 |

In the analysis presented below in Table 10, the patients were separated into two groups—one, positive for TERT C228T/C250T mutation; two, negative for TERT mutation. Compared with group one, group two had a significantly higher association with patient death, demonstrating a significant predictive power of TERT promoter mutation for patient mortality in melanoma.

TABLE 10

| Group number | TERT status | Patient death or not (No.) 1 | Patient death or not (No.) 0 | P value |
|---|---|---|---|---|
| One | 0 | 7 | 12 | |
| Two | 1 | 10 | 2 | 0.025 |

In the analysis presented below in Table 11, the melanoma patients were divided into four groups—one, no mutation at all; two, only BRAF V600E mutation; three, only TERT C228T/C250T mutation; four, coexistence of both TERT C228T/C250T and BRAF V600E. Compared with group one, group two alone or group three alone was not significantly associated with patient mortality, but group four was. In other words, coexistence of TERT promoter and BARF mutations was more significantly associated with patient death. These results thus demonstrate a uniquely higher predictive power of coexistence of TERT promoter and BRAF mutations for poor outcomes (patient death) of melanoma.

TABLE 11

| Group number | BRAF status | TERT status | Patient death or not (No.) 1 | Patient death or not (No.) 0 | P value |
|---|---|---|---|---|---|
| One | 0 | 0 | 5 | 11 | |
| Two | 1 | 0 | 2 | 1 | 0.523 |
| Three | 0 | 1 | 3 | 1 | 0.255 |
| Four | 1 | 1 | 7 | 1 | 0.027 |

Example 3: Diagnostic and Prognostic TERT Promoter Mutations in Thyroid Fine Needle Biopsy Thyroid cancer is a common endocrine malignancy, which has seen a worldwide rapid rise in incidence in recent years (Howlader, et al. 2014; Jemal, et al. 2011). In the United States, there are 62,980 new cases of thyroid cancer and 1,890 deaths from this cancer estimated for 2014 (Howlader et al. 2014). The diagnosis of thyroid cancer typically starts from the evaluation of thyroid nodules, which are extremely common, seen in approximately 5-10% of adult people on physical examination and 50-70% of people over the age of 60 years on ultrasonography (Guth, et al. 2009; Mazzaferri 1993). Clinical evaluation of thyroid nodules for malignancy is therefore a major task in the practice of thyroid medicine, in which a diagnostic mainstay is fine needle aspiration biopsy (FNAB). FNAB is accurate in most patients in that it can provide a reliable diagnosis of benign or malignant thyroid tumor (Bose and Walts 2012). In about 25-30% of cases, however, FNAB yields indeterminate cytological findings, leaving the diagnosis of thyroid nodules in this group in dilemma. With an overall risk of about 25% for malignancy associated with the indeterminate cytology on FNAB, patients in this group are conventionally recommended for thyroidectomy and, as a result, most of these patients have to sacrifice their thyroid glands for benign thyroid tumors (Cooper, et al. 2009). Along with this diagnostic challenge of thyroid nodules, there are also prognostic issues with thyroid cancer. Although thyroid cancer in most patients is indolent with an excellent prognosis, some cases seem to be destined for poor prognosis with increased disease recurrence and patient mortality. Risk stratification for prognostication of thyroid cancer has been conventionally based on clinicopathological risk factors, which are often inaccurate and preoperatively unavailable.

In recent years, molecular-based diagnostic and prognostic approaches for thyroid cancer have been extensively investigated and some molecular markers have been identified and proven to be clinically useful (Xing, et al. 2013b). These include diagnostically the gene expression classifier (Alexander, et al. 2012), genetic marker panel (Nikiforov, et al. 2011) and galctin-3 (Bartolazzi, et al. 2008) and prognostically BRAFV600E mutation (Xing, et al. 2014a; Xing, et al. 2013a). The diagnostic and prognostic accuracy of these markers, however, still have much room for improvement and new markers are needed to this end.

Two recently discovered TERT promoter mutations in thyroid cancer provide great promises in this regard—chr5: 1,295,228C>T and chr5:1,295,250C>T (termed here as C228T and C250T, respectively), which represent nucleotide changes of −124 C>T and −146 C>T from the ATG translation start site of the TERT gene, respectively. These mutations play an important role in human cancer by increasing the transcriptional activities of the TERT promoter (Horn, et al. 2013; Huang, et al. 2013). Our group reported the first study on these two mutations in thyroid cancer (Liu, et al. 2013), in which we found a prevalence of mutations of 0.0% (0/85), 11.7% (30/257), 13.9% (11/79), 37.5% (3/8), and 46.3% (25/54) in benign thyroid tumors, papillary thyroid cancers (PTC), follicular thyroid cancer (FTC), poorly differentiated thyroid cancers, and anaplastic thyroid cancer (ATC), respectively. This study demonstrated an exclusive occurrence of TERT promoter mutations in thyroid cancer but not in benign thyroid tumors and also their association with poor clinicopathological characteristics of thyroid cancer. These findings were confirmed in our and others' subsequent studies (Liu, et al. 2014; Melo, et al. 2014; Vinagre, et al. 2013). As described herein, we demonstrated that TERT promoter and BRAF V600E mutations cooperatively identify the most aggressive PTC with the highest recurrence (Xing, et al. 2014b). These studies strongly suggest that TERT promoter mutations are potential novel diagnostic and prognostic biomarkers for thyroid cancer. Here, we performed the first study to directly evaluate the value of preoperatively testing TERT promoter mutations on thyroid FNAB specimens in the diagnostic evaluation of thyroid nodules and preoperative prognostic evaluation of thyroid cancer.

Materials and Methods

FNAB samples and DNA preparation. Three hundred and eight FNAB specimens were obtained preoperatively by FNAB to thyroid nodules in 308 patients who underwent thyroidectomy for established thyroid cancer, cytologically indeterminate thyroid nodules or symptomatic goiter as described previously (Xing, et al. 2009; Xing, et al. 2004). Genomic DNA from FNAB specimens was isolated using standard procedures of protease K digestion, phenol—chloroform extraction, and ethanol precipitation. The study was conducted based on an institutional review board-approved protocol and written informed patient consents were obtained where appropriate.

Genomic DNA sequencing to identify TERT promoter and BRAF V600E mutations. Standard polymerase chain reaction (PCR) was performed for direct genomic DNA sequencing to identify TERT promoter mutations (See Liu et al. 2013). Briefly, a fragment of the TERT promoter, which contained the sites for TERT promoter mutations C228T and C250T, was amplified by PCR on genomic DNA from FNAB specimens using primers 5' AGTGGAT-TCGCGGGCACAGA 3'(sense) (SEQ ID NO:2) and 5' CAGCGCTGCCTGAAACTC 3'(antisense) (SEQ ID NO:3). PCR of standard reaction mixture containing about 40-50 ng genomic DNA/reaction was performed with an initial denaturation at 95° C. for 3 min, followed by 10 cycles of 95° C. denaturation for 30 seconds, 55° C. annealing for 30 seconds, and 68° C. elongation for 1 min. This was then followed by 30 cycles of the same settings except for the elongation for additional 5 seconds in each cycle and the completion with an elongation at 68° C. for 7 min. Quality confirmation of the PCR products was achieved by gel electrophoresis and sequencing PCR was performed using a Big Dye terminator v3.1 cycle sequencing reaction kit (Applied Biosystems) and an ABI PRISM 3730 automated next generation genetic analyzer (Applied Biosystems) at our institutional sequencing facility.

Identification of the BRAF V600E mutation was similarly achieved by direct genomic DNA sequencing (See Xing, et al. 2005). Briefly, PCR was performed to amplify exon 15 of the BRAF gene containing the site for the T1799A (V600E) mutation using primers TCATAATGCTTGCTCTGA-TAGGA (sense) (SEQ ID NO:4) and GGCCAAAAATT-TAATCAGTGGA (antisense) (SEQ ID NO:5). This resulted in a 212-bp PCR product. The PCR settings included one cycle of 95° C. for 5 min; two cycles of 95° C. for 1 min, 60° C. for 1 min, and 72° C. for 1 min; two cycles of 95° C. for 1 min, 58° C. for 1 min, and 72° C. for 1 min; 35 cycles of 95° C. for 1 min, 56° C. for 1 min, and 72° C. for 1 min, followed by an extension at 72° C. for 5 min. After quality confirmation by gel electrophoresis, the PCR products were subjected to Big Dye reaction and sequencing analysis.

Diagnostic potential of testing thyroid FNAB specimens for TERT promoter mutations. We analyzed the status of the two TERT promoter mutations and BRAF V600E mutation on 308 FNAB specimens obtained preoperatively from 308 patients with confirmed postoperative pathological diagnosis of the biopsied thyroid nodules. These included 111 PTC, 18 FTC, and 179 benign thyroid nodules (including 111 cases of adenomas, 55 cases of multinodular hyperplasia, and 13 cases of Hashimoto's thyroiditis). As shown in Table 12, no TERT promoter mutation was found in any of the 179 benign thyroid nodules. TERT promoter mutations C228T and C250T were found in 9 cases of thyroid cancers, including 5 PTC and 4 FTC, with a collective prevalence of 7.0% (9/129) in thyroid cancers, which was slightly lower than the reported prevalence in these cancers (Liu et al. 2013; Liu et al. 2014; Melo et al. 2014; Vinagre et al. 2013), likely reflecting the compromised detection sensitivity of direct genetic sequencing on often sparse FNAB specimens as addressed previously (Xing et al. 2004). The BRAF V600E mutation was found solely in thyroid nodules of PTC, being 37.8% (42/111), which was slightly lower than the prevalence of this mutation generally seen in PTC (Xing 2005; Xing 2007), again reflecting an under detection by direct genetic sequencing on FNAB specimens (Xing et al. 2004). There were two cases of BRAF V600E-positive PTC that additionally harbored TERT promoter mutations, with one harboring TERT C228T and the other harboring TERT C250T. If any mutation was counted, the collective prevalence of TERT promoter and BRAF V600E mutations was 40.5% (45/111) in thyroid nodules of PTC. When thyroid nodules of PTC and FTC were collectively analyzed, BRAF V600E was found in 32.6% (42/129) and TERT promoter and BRAF mutations were collectively found in 38.0% (49/129) of the cases. Based on these results, the diagnostic specificity of TERT promoter mutations on FNAB specimens for thyroid cancer was 100% and sensitivity 7.0%. When TERT promoter mutations were used in combination with BRAF V600E, the diagnostic specificity remained to be 100% and the sensitivity rose to 38.0%. This also represented an increase from the diagnostic sensitivity of 32.6% when BRAF mutation alone was used (Table 12). Three cases of the TERT promoter mutation-positive thyroid nodules of FTC showed indeterminate cytological findings on FNAB. Thus preoperative testing for TERT promoter mutations on FNAB could help make a definitive diagnosis of thyroid cancer in these cases of thyroid nodules.

TABLE 12

| Thyroid conditions | TERT C228T mutation, n/N (%) | TERT C250T mutation, n/N (%) | Two TERT mutations collectively | BRAF V600E mutation, n/N (%) | Any mutation** |
|---|---|---|---|---|---|
| Benign thyroid nodules* | 0/179 (0) | 0/179 (0) | 0/179 (0) | 0/179 (0) | 0/179 (0) |
| PTC | 4/111 (3.6) | 1/111 (0.9) | 5/111 (4.5) | 42/111 (37.8) | 45/111 (40.5) |
| FTC | 3/18 (16.7) | 1/18 (5.6) | 4/18 (22.2) | 0/18 (0) | 4/18 (22.2) |
| PTC + FTC | 7/129 (5.4) | 2/129 (1.6) | 9/129 (7.0) | 42/129 (32.6) | 49/129 (38.0) |

Footnotes
*Benign thyroid nodules included 111cases of adenomas, 55 cases of multinodular hyperplasia, and 13cases of Hashimoto's thyroiditis.
**One case of PTC harbored both TERT C228T and BRAF V600E mutations and another harbored both TERT C250T and BRAF V600E mutations.
PTC, papillary thyroid cancer;
FTC, follicular thyroid cancer.

Results

Prognostic potential of preoperatively testing thyroid FNAB specimens for TERT promoter mutations. The TERT promoter mutation-positive thyroid nodules mostly were thyroid cancers that exhibited aggressive clinicopathological outcomes, such as lymph node metastases, extrathyroidal invasion, distant metastases, tumor recurrence or even patient death. Four of the five patients with TERT promoter mutation-positive thyroid nodules of PTC had such outcomes. Specifically, patient 1 (MX225), positive on preoperative FNAB for TERT C228T, was a 51-year-old man, in whom thyroidectomy revealed a 2.0-cm PTC in the right thyroid lobe with extrathyroidal invasion and metastases in 20/85 neck lymph nodes. Patient 2 (MX 249), positive on preoperative FNAB for TERT C228T, was also a 51-year-old man, in whom thyroidectomy revealed a 3.5 cm tumor with mixed PTC and ATC in the left thyroid lobe with extrathyroidal invasion and metastases in 11 of 18 lymph nodes. Post-surgery imaging showed extensive metastases in the lungs. He died one year after the initial diagnosis. Patient 3 (MX279), positive on preoperative FNAB for both the TERTC228T and BRAF V600E mutations, was a 54-year-old man, in whom thyroidectomy revealed a 2.5-cm PTC with tall cell component in the right thyroid lobe, with metastases in 7/16 lymph nodes and invasion to trachea, requiring tracheotomy. He had metastatic recurrence to the right posterior ilium and the lungs at the follow-up of 31 months after the initial treatments, which were radioiodine non-avid. Patient 4 (MX466), positive on preoperative FNAB both for TERT C250T and BRAF V600E, was a 74-year-old man, in whom thyroidectomy revealed multifocal PTC with the largest being 3.0 cm in the left thyroid lobe with vascular invasion and metastases in 4 of 11 lymph nodes. Even with radioiodine ablation after thyroidectomy, thyrotropin-stimulated thyroglobulin rose to 3.0 ng/mL 38 months after the initial treatments, which was undergoing further diagnostic evaluations at the time of this writing. Patient 5 (MX525), positive for TERT C228T mutation on preoperative FNAB, was a 47-year-old man, in whom thyroidectomy revealed a 2.5-cm PTC in the right thyroid lobe without lymph node removal. He continued to be doing well with no apparent disease recurrence 55 months after the initial treatments. The two cases of patients with coexisting TERT promoter and BRAF V600E mutations both had disease recurrence.

Three of the four patients with TERT promoter mutation-positive thyroid nodules of FTC exhibited poor clinicopathological outcomes. Specifically, patient 1 (MX39), positive on preoperative FNAB for TERT C228T, was a 54-year-old woman, in whom thyroidectomy revealed a worrisome large FTC of 6.5 cm and she is currently clinically followed. Patient 2 (MX66), positive on preoperative FNAB for TERT C250T, was a 77-year-old man, in whom thyroidectomy reveled a 8.0-cm FTC in the left thyroid lobe, with gradually rising serum thyroglobulin in the subsequent years, and a 6.0-cm recurrent FTC in the left neck as well as lungs metastases were found 11 years after the initial treatments. Patient 3 (MX238), positive for TERTC228T mutation on preoperative FNAB, was a 74-year-old man, in whom thyroidectomy revealed a 5.0-cm FTC in the right thyroid lobe with extensive extrathyroidal and vascular invasion. Post-radioiodine therapy body scan showed wide bony metastasis to clivus in the skull base, sternum, proximal right upper extremity, right proximal humerus, thoracic and lumbar spine, a left posterior inferior rib, right scapula, pelvis, and bilateral femurs. The patient died from extensive FTC metastases 10 months after the initial diagnosis and treatments. Patient 4 (MX488), positive on preoperative FNAB for TERT C250T, was a 67-year-old woman, in whom thyroidectomy revealed a 1.5-cm FTC in the left thyroid lobe with no recurrence at 32 months of follow-up after the initial treatments.

Overall, seven of nine (78%) thyroid cancer patients who were TERT promoter mutation-positive on preoperative FNAB testing of the thyroid nodules exhibited aggressive tumor behaviors and poor clinical outcomes, including disease recurrence and patient deaths in several cases. This represents a poorer prognosis than generally seen with PTC and FTC.

Discussion

This is the first study directly investigating the diagnostic and prognostic potentials of preoperatively testing on thyroid FNAB specimens for the recently discovered TERT promoter mutations in thyroid cancer. The prevalence of TERT promoter mutations in differentiated thyroid cancer (PTC and FTC) found in the present study was slightly lower than the generally reported prevalence in primary tumors, reflecting an expected underestimate on mutation testing by direct DNA sequencing on FNAB specimens (Xing et al. 2004). This test sensitivity can be expected to be improved by using more sensitive testing modalities, such as the Mutector colorimetic assay (Xing et al. 2009; Xing et al. 2004) or the real-time Light Cycler PCR and fluorescence melting curve analysis (Nikiforov et al. 2011). Nevertheless, the present study principally demonstrates the feasibility of testing TERT promoter mutations on routine FNAB specimens. Compared with the BRAF V600E mutation, the prevalence of TERT promoter mutations is relatively low in thyroid cancer. Thus, the diagnostic sensitivity of TERT promoter mutation testing alone on FNAB is low. The sensitivity, however, could be increased when TERT promoter mutations are used in combination with other diagnostic molecular markers. This may be true particularly when more sensitive testing methods are used and TERT promoter mutations are tested in conjunction with the currently known molecular markers, such as BRAF mutation, RAS mutation, and RET-PTC and PAX8/PPARγ rearrangements, which had a sensitivity of close to 90% for thyroid nodules of indeterminate cytology on FNAB (Nikiforov et al. 2011). The present study already demonstrated that addition of TERT promoter mutations could increase the diagnostic sensitivity of BRAF V600E mutation for thyroid cancer and were helpful in making a definitive diagnosis of thyroid cancer in some cases of cytologically indeterminate thyroid nodules. Thus, it is expectable that inclusion of TERT promoter mutations would improve the diagnostic sensitivity of the currently used panel of diagnostic genetic molecular markers for thyroid cancer (Nikiforov et al. 2011), likely brining the sensitivity to above 90%. It is also possible that addition of TERT promoter mutations may improve the diagnostic values of the gene expression classifier (Alexander et al. 2012) and galectin-3 (Bartolazzi et al. 2008). Importantly, in a large number of benign FNAB specimens, we found no TERT promoter mutation, consistent with the similar findings in primary tumors in several recent studies (Liu et al. 2013; Liu et al. 2014; Melo et al. 2014; Vinagre et al. 2013), thus demonstrating a 100% diagnostic specificity. This means that a positive TERT promoter mutation test result on FNAB makes a definitive diagnosis of thyroid cancer. Therefore, testing of TERT promoter mutations on FNAB, particularly when used in conjunction with testing of the currently established molecular markers, will most likely have a useful diagnostic value that may improve the current diagnostic evaluation of thyroid nodules.

Several studies demonstrated an association of TERT promoter mutations with aggressive clinicopathological characteristics (Liu et al. 2013; Liu et al. 2014; Melo et al.

2014; Xing et al. 2014b). Consistent with these studies on primary tumors, the present study demonstrated that TERT promoter mutation-positive thyroid nodules were not only 100% malignant tumors but these cancers mostly also behaved aggressively. Seven of the nine (78%) TERT promoter mutation-positive thyroid nodules turned out to be aggressive cancers with multiple aggressive clinicopathological behaviors, including lymph node metastasis, extrathyroidal and local invasion, distant metastasis, tumor recurrence or patient deaths. In a cohort of 507 cases of PTC patients, we recently demonstrated that coexistence of TERT promoter and BRAF mutations was associated with particularly aggressive clinicopathological outcomes of PTC, including a dramatically increased recurrence risk (Xing et al. 2014b). To be consistent with these findings, the present study found two such cases of PTC with dual mutations, both of which had aggressive tumor behaviors and disease recurrence. The present results on directly testing TERT promoter mutations on FNAB specimens provide the first direct evidence demonstrating the prognostic potential of preoperatively testing these mutations for thyroid cancer—a positive result of TERT promoter mutations predicts preoperatively poorer clinicopathological outcomes of thyroid cancer. Such a positive preoperative TERT promoter mutation test result would favor more aggressive treatments of the patients, such as more aggressive initial thyroid surgery and subsequent more vigilant monitoring for disease recurrence.

In summary, this is the first study of preoperatively testing TERT promoter mutations along with BRAF V600E on FNAB, demonstrating strong diagnostic and prognostic potentials of this novel molecular test for thyroid cancer. The results provide important evidence supporting the inclusion of TERT promoter mutations in the currently used thyroid molecular testing to assist the diagnosis of thyroid nodules and preoperative risk stratification for better management of thyroid cancer.

REFERENCES

1. Alexander E K, Kennedy G C, Baloch Z W, Cibas E S, Chudova D, Diggans J, Friedman L, Kloos R T, LiVolsi V A, Mandel S J, et al. 2012 Preoperative diagnosis of benign thyroid nodules with indeterminate cytology. *New England Journal of Medicine* 367 705-715.
2. Bartolazzi A, Orlandi F, Saggiorato E, Volante M, Arecco F, Rossetto R, Palestini N, Ghigo E, Papotti M, Bussolati G, et al. 2008 Galectin-3-expression analysis in the surgical selection of follicular thyroid nodules with indeterminate fine-needle aspiration cytology: a prospective multicentre study. *Lancet Oncology* 9 543-549.
3. Bose S & Waits A E 2012 Thyroid fine needle aspirate: a post-Bethesda update. *Adv Anat Pathol* 19 160-169.
4. Cooper D S, Doherty G M, Haugen B R, Kloos R T, Lee S L, Mandel S J, Mazzaferri E L, McIver B, Pacini F, Schlumberger M, et al. 2009 Revised American Thyroid Association management guidelines for patients with thyroid nodules and differentiated thyroid cancer. *Thyroid* 19 1167-1214.
5. Guth S, Theune U, Aberle J, Galach A & Bamberger C M 2009 Very high prevalence of thyroid nodules detected by high frequency (13 MHz) ultrasound examination. *European Journal of Clinical Investigation* 39 699-706.
6. Horn S, Figl A, Rachakonda P S, Fischer C, Sucker A, Gast A, Kadel S, Moll I, Nagore E, Hemminki K, et al. 2013 TERT promoter mutations in familial and sporadic melanoma. *Science* 339 959-961.
7. Howlader N, Noone A M, Krapcho M, Garshell J, Miller D, Altekruse S F, Kosary C L, Yu M, Ruhl J, Tatalovich Z, et al. 2014 SEER Cancer Statistics Review, 1975-2011, National Cancer Institute. Bethesda, Md., http://seer.cancer.gov/csr/1975_2011/, based on November 2013 SEER data submission, posted to the SEER web site, April 2014.
8. Huang F W, Hodis E, Xu M J, Kryukov G V, Chin L & Garraway L A 2013 Highly recurrent TERT promoter mutations in human melanoma. *Science* 339 957-959.
9. Jemal A, Bray F, Center M M, Ferlay J, Ward E & Forman D 2011 Global cancer statistics. *CA: A Cancer Journal for Clinicians* 61 69-90.
10. Liu X, Bishop J, Shan Y, Pai S, Liu D, Murugan A K, Sun H, El-Naggar A K & Xing M 2013 Highly prevalent TERT promoter mutations in aggressive thyroid cancers. *Endocrine-Related Cancer* 20 603-610.
11. Liu X, Qu S, Liu R, Sheng C, Shi X, Zhu G, Murugan A K, Guan H, Yu H, Wang Y, et al. 2014 TERT promoter mutations and their association with BRAF V600E mutation and aggressive clinicopathological characteristics of thyroid cancer. *Journal of Clinical Endocrinology and Metabolism* 99 E1130-1136.
12. Mazzaferri E L 1993 Management of a solitary thyroid nodule. *N Engl J Med* 328 553-559.
13. Melo M, da Rocha A G, Vinagre J, Batista R, Peixoto J, Tavares C, Celestino R, Almeida A, Salgado C, Eloy C, et al. 2014 TERT promoter mutations are a major indicator of poor outcome in differentiated thyroid carcinomas. *Journal of Clinical Endocrinology and Metabolism* 99 E754-765.
14. Nikiforov Y E, Ohori N P, Hodak S P, Carty S E, LeBeau S O, Ferris R L, Yip L, Seethala R R, Tublin M E, Stang M T, et al. 2011 Impact of mutational testing on the diagnosis and management of patients with cytologically indeterminate thyroid nodules: a prospective analysis of 1056 FNA samples. *Journal of Clinical Endocrinology and Metabolism* 96 3390-3397.
15. Vinagre J, Almeida A, Populo H, Batista R, Lyra J, Pinto V, Coelho R, Celestino R, Prazeres H, Lima L, et al. 2013 Frequency of TERT promoter mutations in human cancers. *Nature Communications* 4 2185.
16. Xing M, Alzahrani A S, Carson K A, Shong Y K, Kim T Y, Viola D, Elisei R, Bendlova B, Yip L, Mian C, et al. 2014a Association between BRAF V600E mutation and recurrence of papillary thyroid cancer. *Journal of Clinical Oncology* [In press].
17. Xing M, Alzahrani A S, Carson K A, Viola D, Elisei R, Bendlova B, Yip L, Mian C, Vianello F, Tuttle R M, et al. 2013a Association between BRAF V600E mutation and mortality in patients with papillary thyroid cancer. *JAMA—Journal of the American Medical Association* 309 1493-1501.
18. Xing M, Clark D, Guan H, Ji M, Dackiw A, Carson K A, Kim M, Tufaro A, Ladenson P, Zeiger M, et al. 2009 BRAF mutation testing of thyroid fine-needle aspiration biopsy specimens for preoperative risk stratification in papillary thyroid cancer. *Journal of Clinical Oncology* 27 2977-2982.
19. Xing M, Haugen B R & Schlumberger M 2013b Progress in molecular-based management of differentiated thyroid cancer. *Lancet* 381 1058-1069.
20. Xing M, Liu R, Liu X, Murugan A K, Zhu G, Zeiger M A, Pai S & Bishop J 2014b BRAF V600E and TERT Promoter Mutations Cooperatively Identify the Most Aggressive Papillary Thyroid Cancer With Highest Recurrence. *Journal of Clinical Oncologypii*: JCO. 2014.55.5094. [Epub ahead of print].

21. Xing M, Tufano R P, Tufaro A P, Basaria S, Ewertz M, Rosenbaum E, Byrne P J, Wang J, Sidransky D & Ladenson P W 2004 Detection of BRAF mutation on fine needle aspiration biopsy specimens: a new diagnostic tool for papillary thyroid cancer. *Journal of Clinical Endocrinology and Metabolism* 89 2867-2872.
22. Xing M, Westra W H, Tufano R P, Cohen Y, Rosenbaum E, Rhoden K J, Carson K A, Vasko V, Larin A, Tallini G, et al. 2005 BRAF mutation predicts a poorer clinical prognosis for papillary thyroid cancer. *Journal of Clinical Endocrinology and Metabolism* 90 6373-6379.
23. Xing M 2005BRAF mutation in thyroid cancer. *Endocrine-Related Cancer* 12 245-262.
24. Xing M 2007BRAF mutation in papillary thyroid cancer: pathogenic role, molecular bases, and clinical implications. *Endocrine Reviews* 28 742-762.

Example 4: TERT Promoter and BRAF Mutations Cooperatively Promote Papillary Thyroid Cancer-related Mortality TERT C228T promoter mutation represents a novel genetic mechanism in thyroid tumorigenesis with promising prognostic potential, but its specific prognostic value in thyroid cancer patient mortality has not been well established. This study explored the role of TERT C228T mutation in papillary thyroid cancer (PTC)-related mortality with respect to the BARF V600E mutation status.

Method. TERT promoter mutation C228T and BRAF V600E were examined by Sanger sequencing of genomic DNA of PTC and their relationship with PTC-related patient death was analyzed.

Results. Among 609 patients (436 females and 173 males, aged 46.1±14.1 years), TERT C228T and BRAF V600E mutations were found in 66 (10.8%) and 225 (36.9%) cases, respectively, and patient death occurred in 18 (3.0%) cases. Death occurred in 13/225 (5.8%) BRAF mutation-positive vs. 5/384 (1.3%) BRAF-negative cases (P=0.002) and 11/66 (16.7%) TERT mutation-positive vs. 7/543 (1.3%) TERT-negative cases (P<0.001). Death occurred in 2/355 (0.6%) cases without any mutation (N), 5/188 (2.7%) cases with BRAF mutation only (B), 3/29 (10.3%) cases with TERT mutation only (T), and 8/37 (21.6%) cases with both TERT and BRAF mutations (T+B), with corresponding deaths per 1000 person-years (95% CI) of 1.37 (0.34-5.50), 7.49 (3.12-17.99), 18.26 (5.89-56.63), and 58.61 (29.31-117.19). The P values are: B vs. N, 0.052; T vs. N, 0.004; B+T vs. N, <0.001, with corresponding HR (95% CI) of 5.13 (0.93-28.26), 20.03 (3.01-133.14), and 19.22 (3.70-99.86) after adjustment for patient age and sex. Similar results were obtained on the analyses of 464 conventional-variant PTC alone. Co-existence of BRAF and TERT promoter mutations were also strongly associated with the loss of radioiodine avidity of recurrent PTC.

TABLE 13

Association between BRAF V600E or TERT C228T and patient death from papillary thyroid cancer

|  | | BRAF+ | BRAF− | P value | TERT+ | TERT− | P value |
|---|---|---|---|---|---|---|---|
| Total cases, N (%) | 609 | 225 (36.9) | 384 (63.1) |  | 66 (10.8) | 543 (89.2) |  |
| Patient deaths n (%) | 18 (3.0) | 13 (5.8) | 5 (1.3) | 0.002 | 11 (16.7) | 7 (1.3) | <0.001 |

TABLE 14

Mutations and PTC-related mortality—All PTC

| Mutation Status | Deaths, n/N (%) | Deaths per 1000 person-years(95% CI) | Hazard ratios (95% CI) Unadjusted | Hazard ratios (95% CI) Adjusted* |
|---|---|---|---|---|
| No mutation | 2/355 (0.56) | 1.37 (0.34-5.50) | 1.00 | 1.00 |
| BRAF mutation only | 5/188 (2.66) | 7.49 (3.12-17.99) | 4.44 (0.81-24.33) | 5.13 (0.93-28.26) |
| TERT mutation only | 3/29 (10.34) | 18.26 (5.89-56.63) | 14.14 (2.36-84.62) | 20.03 (3.01-133.14) |
| BRAF + TERT mutations | 8/37 (21.62) | 58.61 (29.31-117.19) | 42.80 (9.00-203.50) | 19.22 (3.70-99.86) |

*Adjusted for patient age and sex

TABLE 15

Mutations and PTC-related mortality—Conventional PTC

| Mutation Status | Deaths, n/N (%) | Deaths per 1000 person-years(95% CI) | Hazard ratios (95% CI) Unadjusted | Hazard ratios (95% CI) Adjusted* |
|---|---|---|---|---|
| No mutation | 2/250 (0.80) | 2.03 (0.51-8.12) | 1.00 | 1.00 |
| BRAF mutation only | 4/163 (2.45) | 7.01 (2.63-18.68) | 2.61 (0.43-15.70) | 3.60 (0.58-22.17) |
| TERT mutation only | 2/21 (9.52) | 16.53 (4.13-66.09) | 8.74 (1.23-62.16) | 11.05 (1.43-85.54) |
| BRAF + TERT mutations | 7/30 (23.33) | 56.87 (27.11-119.29) | 26.85 (5.53-130.37) | 17.40 (3.27-92.56) |

*Adjusted for patient age and sex

Conclusions. This large study demonstrates that TERT promoter mutation is strongly associated with PTC-related mortality, particularly when coexisting with BRAF mutation. Coexistence of the two mutations represents a unique genetic background that defines the group of PTC patients with the highest risk for morality.

In addition to the promoting effects of TERT C228T and BRAF V600E mutation on previously examined aggressive clinicopathological outcomes, the two mutations each alone also promoted PTC-related patient mortality. Coexistence of TERT promoter and BRAF mutations synergized their effects on PTC-related mortality. TERT promoter and BRAF mutations cooperatively identify the most aggressive cases of PTC with the highest mortality

I claim:

1. A method for treating a subject having aggressive thyroid cancer comprising the steps of:
   (a) contacting DNA extracted from a biological sample obtained from the subject with (i) at least one primer that specifically hybridizes to the telomerase reverse transcriptase (TERT) gene and (ii) at least one primer that specifically hybridizes to the BRAF gene;
   (b) amplifying by polymerase chain reaction (PCR) (i) a region of the TERT gene that comprises −124 to −146 from the translation start site in the promoter of the TERT gene and (ii) a region of the BRAF gene that comprises nucleotide 1799 from the translation start site of the BRAF gene;
   (c) sequencing the amplification products to detect the presence of a mutation at −124 (C228T) and/or −146 (C250T) from the translation start site in the promoter of the TERT gene and/or a mutation at nucleotide 1799 (T1799A) from the translation start site of the BRAF gene; and
   (d) treating the subject having the C228T and/or C250T mutation and/or the T1799A mutation with a treatment modality appropriate for a subject having aggressive thyroid cancer, wherein the treatment modality is selected from the group consisting of thyroidectomy, hemithyroidectomy, and radioactive iodine therapy.

2. The method of claim 1, wherein the treatment modality further comprises administering to the subject a BRAF inhibitor, wherein the BRAF inhibitor comprises Sorafenib, Vemurafenib, BDC-0879, PLX-4720, Dabrafenib, or LGX818.

3. The method of claim 1, wherein the treatment modality further comprises administering to the subject a MEK inhibitor, wherein the MEK inhibitor comprises trametinib, selumetinib (AZD6244), CI1040, PD0325901, or refametinib.

4. The method of claim 1, wherein the aggressive thyroid cancer is papillary thyroid cancer (PTC) or anaplastic thyroid cancer.

5. A method for identifying a subject as having or likely to develop aggressive thyroid cancer comprising the steps of:
   (a) contacting DNA extracted from a biological sample obtained from the subject with (i) at least one primer that specifically hybridizes to the TERT gene, wherein the at least one primer comprises SEQ ID NO:2 and/or SEQ ID NO:3 and (ii) at least one primer that specifically hybridizes to the BRAF gene, wherein the at least one primer comprises SEQ ID NO:4 and/or SEQ ID NO:5;
   (b) amplifying by PCR (i) a region of the TERT gene that comprises −124 to −146 from the translation start site in the promoter of the TERT gene and (ii) a region of the BRAF gene that comprises nucleotide 1799 from the translation start site of the BRAF gene;
   (c) sequencing the amplification products to detect the presence of a mutation at −124 (C228T) and/or −146 (C250T) from the translation start site in the promoter of the TERT gene and/or a mutation at nucleotide 1799 (T1799A) from the translation start site of the BRAF gene, wherein the detection of the mutation(s) indicates the subject has or is likely to develop aggressive thyroid cancer.

6. The method of claim 5, further comprising the step of administering a treatment modality appropriate for a subject having or likely to develop aggressive thyroid cancer, wherein the treatment modality is selected from the group consisting of thyroidectomy, hemithyroidectomy, and radioactive iodine therapy.

7. The method of claim 6, wherein the treatment modality further comprises administering to the subject a BRAF inhibitor, wherein the BRAF inhibitor comprises Sorafenib, Vemurafenib, BDC-0879, PLX-4720, Dabrafenib, or LGX818.

8. The method of claim 5, wherein the aggressive thyroid cancer is papillary thyroid cancer (PTC) or anaplastic thyroid cancer.

9. The method of claim 6, wherein the treatment modality further comprises administering to the subject a MEK inhibitor, wherein the MEK inhibitor comprises trametinib, selumetinib (AZD6244), CI1040, PD0325901, or refametinib.

10. The method of claim 1, wherein the biological sample is from a fine needle aspiration biopsy.

* * * * *